US006303766B1

(12) United States Patent
Grabau et al.

(10) Patent No.: US 6,303,766 B1
(45) Date of Patent: Oct. 16, 2001

(54) SOYBEAN PHYTASE AND NUCLEIC ACID ENCODING THE SAME

(75) Inventors: Elizabeth A. Grabau; Carla Hegeman, both of Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 09/312,183

(22) Filed: May 14, 1999

(51) Int. Cl.$^7$ .......................... C07H 21/02; C07H 21/04; C12N 15/63; C12N 15/00; A01H 5/00
(52) U.S. Cl. ..................... 536/23.1; 435/320.1; 435/410; 435/69.1; 800/295
(58) Field of Search ........................ 536/23.1; 435/320.1, 435/69.1, 410; 800/295

(56) References Cited

U.S. PATENT DOCUMENTS

| | | | |
|---|---|---|---|
| 5,436,156 | 7/1995 | Van Gorcum et al. | 435/252.3 |
| 5,593,963 | 1/1997 | Van Ooijen et al. | 514/12 |
| 5,633,436 | * 5/1997 | Wandelt | 800/205 |
| 5,780,292 | 7/1998 | Nevalainen et al. | 435/256.8 |
| 5,824,779 | 10/1998 | Koegel et al. | 530/370 |
| 5,824,877 | 10/1998 | Hinchee et al. | 800/205 |
| 5,830,732 | 11/1998 | Mochizuki et al. | 435/195 |
| 5,834,286 | 11/1998 | Nevalainen et al. | 435/196 |
| 5,863,533 | 1/1999 | Van Gorcum et al. | 424/94.6 |
| 5,866,118 | 2/1999 | Berka et al. | 424/94.6 |
| 5,876,997 | 3/1999 | Kretz | 435/196 |

FOREIGN PATENT DOCUMENTS

| | | |
|---|---|---|
| 0 684 313 | 11/1995 | (EP) . |
| 0 897 010 | 2/1999 | (EP) . |
| 0 897 985 | 2/1999 | (EP) . |
| WO 97/48812 | 12/1997 | (WO) . |
| WO 98/06856 | 2/1998 | (WO) . |
| WO 98/20139 | 5/1998 | (WO) . |
| WO 98/28408 | 7/1998 | (WO) . |
| WO 98/28409 | 7/1998 | (WO) . |

OTHER PUBLICATIONS

Ehrlich et al. Annual Meeting of the American Society of Plant Physiologists, Pittsburgh, PA, USA, Aug. 1–5, 1992. Plant Physiol (1992) 99 ( 1 Suppl) 87.*
Hamada. Journal of the American Oil Chemists Society (1996) 73(9) 1143–1151.*
Patel et al. (1996) GENBANK U48448.*
Lange et al. 1994. PNAS USA 91:8552–8556.*
Mullaney and Ullah, "Identification of a histidine acid phosphatase (phyA)–like *Arabidopsis thaliana*". Biochemical and Biophysical Research Communications: 251, 252–255 (1998).
Maugenest et al., "Cloning and characterization of cDNA encoding a maize seedling phytase", Biochem. J. 322: 511–517 (1997).
Maugenest et al., "Structure of two maize phytase genes and their spatio–temporal expression during seedling development". Plant Molecular Biology 39: 503–514 (1999).
Grabau, et al., "Improving phosphorus utilization in soybean meal through phytase gene engineering", 6th Biennial Conference on the Molecular and Cellular biology of the Soybean, University of Missouri, Columbia, MO. Aug. 12–14, 1996 (abstract).
Hegeman and Grabau, "Purification and characterization of a phytate–degrading enzyme from germinating soybean cotyledons". 6th Biennial Conference on the Molecular and Cellular Biology of the Soybean, University of Missouri, Columbia, MO. Aug. 12–14, 1996 (abstract).
Grabua, et al., "Recombinant phytase expression in soybean". International Wordshop of the Biochemistry of Plant Phytate and Phytases, Copenhagen, Denmark, Oct. 25–28, 1997 (abstract).
Grabau, et al., "Strategies for modifying phytic acid content in soybean seeds". 7th Biennial Conference on the Molecular and Cellular biology of the Soybean, University of Tennessee, Knoxville, TN. Jul. 26–29, 1998 (abstract).
Thornburg, et al., "Modification of fungal phytase to include a vacuolar targeting sequence", American society of Plant Physiologist, Southern Section Society, Roanoke, VA. Mar. 21, 1998 (abstract).
Pen, et al.,*Bio/Technology* 11:811–814 (1993).
Li, et al., *Plant Physiol* 114:1103–1111 (1997).
Wyss, et al. *Applied and Environmental Microbiology* 65(2) :367–373 (Feb. 1999).
Gibson and Ullah, "Phytases and Their Action on Phytic Acid" *Inositol Metabolism in Plants*, Wiley Liss, Inc., 77–92 (1990).
Gibson and Ullah, *Archives of Biochemistry and Biophysics* 260(2) :503–513 (Feb. 1997).
Hanlon, et al., "Expression and locationization of fungal phytase in transgenic soybean cells". 7th Biennial Conference on the Molecular and Cellular biology of the Soybean, University of Tennessee, Knoxville, TN. Jul. 26–29, 1998 (abstract).
Verwoerd, et al. *Plant Physiol* 109:1199–1205 (1995).
Wyss, et al., *Applied and Environmental Microbiology* 65(2) : 359–366 (Feb. 1999).
Pasamontes et al.,*Applied and Environmental Microbiology* 63 (5): 1696–1700 (May 1997).

* cited by examiner

*Primary Examiner*—Jeffrey Fredman
*Assistant Examiner*—Juliet C. Einsmann
(74) *Attorney, Agent, or Firm*—Drinker Biddle & Reath LLP

(57) ABSTRACT

Isolated soybean phytase polypeptides and isolated nucleic acids encoding soybean phytases are provided. The invention is also directed to nucleic acid expression constructs, vectors, and host cells comprising the isolated soybean phytase nucleic acids, as well as methods for producing recombinant and non-recombinant purified soybean phytase. The invention also relates to transgenic plants expressing the soybean phytase, particularly expression under seed-specific expression control elements.

20 Claims, 4 Drawing Sheets

SOYBEAN PHYTASE AND NUCLEIC ACID ENCODING THE SAME

REFERENCE TO GOVERNMENT GRANT

This invention was made in the course of research sponsored by the United States Department of Agriculture under grants NRI CGP 97-35504-4297 and/or NRI CGP 94-37500-0681. The U.S. Government may have certain rights in the invention.

1. FIELD OF THE INVENTION

The invention relates to nucleic acids encoding the soybean phytase protein, the soybean phytase per se, and method for obtaining expression of the soybean phytase in appropriate hosts.

2. BACKGROUND OF THE INVENTION

2.1 Phytate

Phosphorous is an essential dietary requirement for animal growth.

Abundant stores of phosphorous are present in plant seeds in the form of phytate (myo-inositol hexakisphosphate). Phytate serves as the storage form of phosphate and myo-inositol for germination and seedling growth. Phytate is synthesized during seed development and comprises 1–3% of the total dry weight of seeds (Reddy et al., *Phytates in Cereals and Legumes*, CRC Press, Inc., Boca Raton, Fla., 1989). In cereals, phytate is deposited in aleurone particles. It is found in protein bodies in legume cotyledons. A biochemical and ultrastructural analysis of soybean seeds showed the presence of phytate in protein bodies, with a significant amount deposited with globoid inclusions (Prattley and Stanley, *J. Food Biochem.* 6:243–253. 1982).

The soybean [*Glycine max* (L.)] has long been recognized as a valuable component of medicine, food and animal feed. Soybean is an important crop worldwide as both a protein and oil source. Soybean is processed to yield soybean oil and soybean meal by a hexane extraction process. Because of its high nutritional value, wide availability, low cost and consistency of composition, soybean meal has displaced most of the animal proteins (meat meal, tankage, and fish meal) and has become a vital component of poultry and swine feeds. Together, poultry and swine feeds account for over two thirds of soybean meal utilization in the United States. Phytate accumulates in soybean during seed development, where it serves a phosphorous storage function. Phytate is normally utilized after germination of the soybean seedling, when it is broken down by newly-synthesized phytase.

Phytate is poorly utilized by humans and other monogastric animals. Because non-ruminant animals lack the enzymes necessary for phytate degradation, phytate-bound phosphorous passes through the gastrointestinal tract undigested, making it unavailable to non-ruminants. Phytate is considered an anti-nutritional factor because it chelates essential minerals such as zinc, manganese, iron, calcium and potassium and forms indigestible protein-phytate complexes (Erdman and Forbes, *J. Am. Oil Chem. Soc.* 58:489–495 (1981); Zhu et al., *Anim. Feed Sci. Techn.* 27:341–351 (1990); Simons et al., *Brit. J. Nutr.* 64:525–540 (1990)). Plant phytate is present predominantly as the calcium-magnesium-potassium salt called phytin. These complex forming properties of phytate are responsible for lowered mineral and protein bioavailability in animal diets containing high phytate levels (Reddy et al., supra).

To meet dietary requirements, inorganic phosphorous is routinely added to swine and poultry rations. Phosphorous supplementation increases feed costs and contributes to the phosphorous content of animal waste. Moreover, non-utilized phytate is excreted by the animals contributes to environmental pollution in areas of intensive animal production. Annually in the United States, swine and poultry generate over 20 million tons of manure containing over 300,000 tons of waste phosphorous (Cromwell and Coffey, Altech Conference Proceedings, 1991). Typically, manure is applied as fertilizer to pastures and croplands, causing an increase in soil phosphorous, eventually resulting in water contamination. Since phosphorous is the limiting nutrient for aquatic plant life growth, increases in water phosphorous content results in eutrophication and decreased water quality. Increased regulatory scrutiny of animal waste disposal has fostered interest in finding solution for decreasing phosphorous output.

2.2 Phytase

Phytases are enzymes that sequentially remove phosphates from the phytate molecule. Phytase (E.C. 3.1.3.8) catalyzes the removal of orthophosphate from various myo-inositol phosphates. Phytases have been characterized from a variety of fungi, bacteria, plants and animals. Fungal phytases are in the general class of acid phosphatases. Numerous studies have shown that supplementation of poultry and livestock feed with microbial phytase improves phosphorus bioavailability (Nelson et al., *Poultry Sci.* 47:1372–1374,1968; Swick and Ivey, *Feed Management* 43:8–17, 1992). Commercially available phytase preparations are derived primarily from the fungus *Aspergillus niger* (originally designated *A. ficuum*) because of high levels of production of this extracellular enzyme (Shieh and Ware, *Appl. Microbiol.* 16:1348–1351, 1968; Ullah, supra). An engineered form of the *A. niger* phytase is now available as a supplement (Natuphos®, BASF). The beneficial effects of supplementation have been demonstrated by the addition of microbial phytase to diets of poultry and swine (Cromwell et al., *J. Anim. Sci.* 73 449–456, 1995; Denbow et al., *Poultry Sci.* 74: 1831–1842, 1995; Potter et al., *Poultry Sci.* 74: 813–820, 1995; Ravindran et al., *Poultry Sci.* 74:1820–1830,1995; Yi et al., *Poultry Sci.* 75:240–249, 1996).

Phytase supplementation reduces the need for inorganic phosphorous and lowers the percentage of dietary phosphorous that is excreted (Yi et al., *Poultry Science* 75:240–249, 1996; Cromwell et al., *J. Animal Science* 73:449–456, 1995). However, commercial phytase supplements are expensive. Moreover, phytase must be added to the feed after pelleting to avoid heat denaturation of the enzyme at the high pelleting temperature.

While phytase occurs naturally in soybean, there is little enzyme activity until seed germination. Hence, phytase is not present in substantial levels in soybean meal. The phytate in soy meal is not utilized by poultry and swine, and passes undigested into manure. The desired timing of phytase expression is during seed development, which would lead to phytase accumulation in the soybean, and soybean meal with reduced phytate.

There have been numerous reports of the isolation and cloning and expression of phytase DNA of non-plant origin. Such sources include ruminal microorganisms (WO 97/48812); *Escherichia coli* B (U.S. Pat. No. 5,876,997); *Thermomyces lanuginosus* (U.S. Pat. No. 5,866,118); *Aspergillus ficum* (U.S. Pat. No. 5,863,533); *Schwanniomy-* ces occidentalis (U.S. Pat. No. 5,840,562); Aspergillus niger var. ALKO243 (U.S. Pat. No. 5,834,286); Schwanniomyces occidentalis (U.S. Pat. No. 5,830,732); Bacillus subtilis (WO 98/06856); Myceliopthora thermophila and Aspergillus terreus (EP 0 684 313); Peniophora lycii (WO 98/28408). U.S. Pat. No. 5,780,292 discloses methods for the overexpression of recombinant Aspergillus niger phytase in the filamentous fungus Trichoderma reesei. U.S. Pat. No. 5,593,963 discloses methods for expression of foreign phytase genes in plants, preferably microbial phytase genes. A heat stable phytase from the fungus Aspergillus fumigatus has been cloned and characterized (Pasamontes et al., Appl. Environ. Microbiol. (1997) 63(5):1696–700).

The cloning and sequencing of the phytase from Aspergillus niger is described in U.S. Pat. No. 5,436,156 to van Gorcom et al. The gene has been introduced into tobacco (Pen et al., Bio/Technology 11:811–814, (1993); Verwood et al., Plant Physiol. 109:1199–1205 (1995)). While feeding trials have demonstrated that transgenic tobacco seeds expressing A. niger were effective as a dietary phytase source in poultry feed, tobacco seeds are expensive to produce and are not normally used as a feedstuff.

Fungal phytase has been expressed in soybean. A study was conducted comparing milled soybean seeds expressing fungal phytase with the commercial Natuphos® preparation as supplements for poultry feeding (Denbow et al., Poultry Sci. 77:878–881, 1998). As measured by body weight gain, phosphorus utilization and phosphorus excretion, the recombinant fungal phytase produced in transgenic soybean was just as effective as Natuphos® as a dietary supplement. However, milled, full-fat soybeans are not generally added to animal diets because of the other anti-nutritional effects of raw soybeans. Soybeans are typically first roasted to eliminate trypsin inhibitors and are then solvent-extracted to yield valuable oil and protein meal fractions. To adhere to normal processing protocols, a phytase transgene should be expressed prior to plant harvest in order to maintain the enzyme's activity needed for break down of seed phytate.

Despite these reports of the cloning of numerous fungal and bacterial phytase genes, the only cloned plant phytase gene reported to date has been from maize (Maugenest et al., Biochem. J. 322:511–517, 1997).

What is needed is a method to increase phosphorous availability in crops, and in soybeans used for animal feed in particular. What is needed is a method to maximize the growth of animals fed a diet which includes soybean, while at the same time lowering the phosphorous content of waste. Desirably, these goals should be achieved without the need for expensive phytase supplements. Specifically, what is needed is a method for decreasing the phytate content of soybean meal by decreasing the phytate content of soybean seeds used for the preparation of meal. Lowered soybean phytate would increase the availability of phosphorous to the animal, lower excretion of phytate into manure, and decrease the associated environmental phosphorous pollution. A decreased phytate level will also increase nutrient utilization of minerals and proteins in soybean meal.

To accomplish these objectives, a method for expressing a phytase gene in soybean seeds is required.

For engineering expression of phytase in soybeans, use of the endogenous soybean phytase gene has distinct advantages over foreign phytase genes, such as bacterial and fungal phytase genes. The soybean enzyme should contain the necessary signals for proper localization of the enzyme to the protein bodies. The soybean phytase is optimally suited to digestion of soybean phytate. Indeed, this is the role of phytase during seed germination. Also, engineered expression of the endogenous gene avoids concerns over the introduction of microbial genes into plants. Despite these advantages, there have been no reports of the successful cloning and expression of the soybean phytase gene.

The direct value of an engineered phytase gene to obtain phytase expression in the soybean would result in reduced costs of phosphorous supplementation in animal feed. The estimate cost of inorganic phosphorous which would be saved is $6.60 per metric ton for a standard soybean-corn meal diet. See, Swick et al., "The Value of Improving Phosphorous Retention", Feed Management 43:8–17 (1992). This does not take into account the additional nutritional value derived from soybean meal resulting from the breakdown of phytate, which acts as an anti-nutritional factor.

2.3 Soybean Phytase Protein

There have been reports claiming purification of a soybean phytase. Stuardi and Buckle, J. Food Biochemistry 10:197–216, 1986 purported to characterize a soybean phytase. However, the purification method utilized by these authors yielded only a partial purification (approximately 100-fold) with recovery of only 28% of the original activity. No sequence analysis was presented.

Gibson and Ullah, Arch. Biochem. Biophys. 260:503–513 (1988), reported purification of soybean phytase via ammonium sulfate precipitation, cationic exchange chromatography, gel filtration, and chromatofocusing. They published partial amino acid sequence data from their purified protein (Gibson and Ullah, "Phytases and their action on phytic acid" In: Inositol Metabolism in Plants, Wiley-Liss, pp. 77–92.1990), which proved to be from a soybean β-amylase, not soybean phytase.

A substantially purified preparation of soybean phytase would have utility as an immunogen for the preparation of antibodies against that enzyme. A purified or partially purified preparation of the enzyme would be useful as a feed or food additive.

Crops engineered to express an elevated concentration of soybean phytase in tissues are useful in the preparation of additives and supplements, as a source of phytase in the preparation of such materials. In particular, soybean plants engineered to constitutively express phytase in seeds is a convenient source of phytase.

3. SUMMARY OF THE INVENTION

It is an object of the invention to provide purified soybean phytase and nucleotide sequences encoding soybean phytase.

It is an object of the invention to provide for the expression of soybean phytase nucleotide sequences in appropriate host cells, to permit the recombinant production of soybean phytase.

It is an object of the invention to provide for the expression of the soybean phytase nucleotide sequence in plant hosts, particularly in the soybean plant, and most particularly in the seeds of the soybean plant, i.e., in the soybeans per se.

It is an object of the invention to provide soybeans, and human and animal food products prepared from soybeans, which contain reduced levels of phytate through expression of phytase genes in soybeans.

It is an object of the invention to provide feed and food additives which comprise soybean phytase.

These and other objects of the invention are apparent from the disclosure which follows.

Isolated nucleotide sequences are provided that encode a soybean phytase. By "isolated" with respect to a soybean phytase nucleotide sequence is meant a nucleotide sequence, e.g., DNA or RNA molecule, that is not immediately contiguous with the 5' and 3' flanking sequences with which the subject sequence is normally contiguous when present in the naturally occurring genome of the soybean plant. The term thus includes, for example, a vector such as a plasmid or viral vector; a nucleic acid that is incorporated into the genome of a heterologous cell (or the genome of a homologous cell, but at a site different from that at which the nucleic acid naturally occurs, or proximal to flanking sequences which do not normally flank the nucleic acid in the natural state); and a polynucleotide that exists as a separate molecule, e.g., a DNA fragment produced by polymerase chain reaction (PCR) amplification or restriction enzyme digestion, or an RNA molecule produced by in vitro transcription. The term also includes a recombinant nucleic acid that forms part of a hybrid gene encoding additional polypeptide sequences that can be used, for example, in the production of a fusion protein.

According to another embodiment of the invention, an isolated nucleotide sequence is provided encoding a polypeptide comprising the amino acid sequence SEQ ID NO:2, SEQ ID NO:3, or fragment of SEQ ID NO:3 having phytase activity.

According to another embodiment of the invention, an isolated nucleotide sequence is provided comprising a soybean phytase coding sequence. By "coding sequence" is meant the nucleotide sequence within a nucleic acid that when transcribed and translated will give rise to a subject amino acid sequence, i.e., exon regions in genomic DNA (gDNA) that when transcribed into mRNA will direct translation of the subject amino acid sequence, or the region from the translation initiation codon to the termination codon in complementary DNA (cDNA). The term "encoded" is used to mean an amino acid sequence coded for in the triplet code of nucleotides by the coding region nucleotide sequence. According to one embodiment, such an isolated nucleotide sequence is selected from the group consisting of:

(a) SEQ ID NO:1;

(b) a nucleotide sequence complementary to SEQ ID NO:1;

(c) a subsequence of SEQ ID NO:1 encoding a polypeptide having phytase activity;

(d) a nucleotide sequence capable of hybridizing under conditions of medium stringency with (a) or (b), or with a probe comprising at least 100 continuous nucleotides of (a) or (b); and (e) a homologous nucleotide sequence which is at least about 60% homologous with (a) or (b).

By "subsequence" is meant a shorter continuous sequence subsumed within a longer sequence. Thus, "subsequence" is synonymous with "fragment" as used for nucleic acids.

According to another embodiment of the invention, an isolated nucleotide sequence is provided comprising a soybean phytase promoter sequence. By "promoter subsequence" is meant a DNA regulatory region capable of binding RNA polymerase in a cell and initialing transcription of a downstream (3' direction) coding sequence. According to one embodiment, such an isolated nucleotide comprises a member selected from the group consisting of:

(a) SEQ ID NO:20;

(b) a nucleotide sequence complementary to SEQ ID NO:20;

(c) a nucleotide sequence capable of hybridizing under conditions of medium stringency with (a) or (b), or with a probe comprising at least 100 continuous nucleotides of (a) or (b); and (d) a homologous nucleotide sequence which is at least about 60% homologous with (a) or (b).

According to another embodiment of the present invention, an isolated soybean phytase is provided. In one embodiment, the phytase molecule comprises the amino acid sequence of SEQ ID NO:2, SEQ ID NO:3, functional derivative of either SEQ ID NO:2 or SEQ ID NO:3, or fragment of SEQ ID NO:3 having phytase activity. By "functional derivative thereof" is meant a derivative of the indicated polypeptide which has the functional characteristics of that polypeptide. Such functional derivatives include naturally occurring, synthetically or recombinantly produced polypeptides, mutants or variants thereof which may have one or more amino acid deletions, substitutions or additions which may have the general characteristics of the phytase of SEQ ID NO:2 or SEQ ID NO:3.

By "isolated" with respect to a "protein" or "polypeptide", e.g., a phytase, is meant that the protein or polypeptide has been synthesized or at least partially purified from its natural state. The term is intended to distinguish the molecule in question from the impure state in which the molecule exists in nature, and encompasses all other forms. In particular, with respect to an "isolated phytase" is meant a polypeptide or protein having phytase activity, or precursor thereof, and which is essentially free of other non-phytase polypeptides, e.g., at least about 40% pure, preferably at least about 60% pure, more preferably at least about 80%, pure, even more preferably at least about 90% pure, as determined by SDS-PAGE.

It should be noted that the above definition of "an isolated polypeptide" also includes fused polypeptides or cleavable fusion polypeptides in which another polypeptide is fused at the N-terminus or the C-terminus of the polypeptide or fragment thereof. A fused polypeptide is produced by fusing a nucleic acid sequence (or portion thereof) encoding another polypeptide to the nucleic acid sequence (or portion thereof) of the present invention. Techniques of producing fusion polypeptides are known in the art, and include, ligating the coding sequence encoding the polypeptides so that they are in frame and that expression of the fused polypeptide is under control of the same promoter(s) and terminator. The expression "isolated polypeptide" also embraces precursors of mature polypeptides, as well as the mature polypeptide. It also embraces glycosylated and non-glycosylated forms, unless otherwise indicated.

By "soybean phytase" is meant a phytase purified from any part of the soybean plant, or a recombinant phytase generated by expression of nucleic acid obtained or derived from soybean. By "recombinant" means produced from cells transformed by an exogenous DNA construct encoding the desired product. Thus, the invention includes both soybean phytase purified from native sources, and soybean phytase peptides and proteins obtained through recombinant production by expression of nucleic acid sequences encoding such phytases. The latter may be glycosylated or nonglycosylated. Preferably, recombinant expression is obtained in a plant host, which results in glycosylated phytase forms. The term "soybean phytase" includes all allelic variations and mutants of phytase derived from soybean plants, as well as fragments of such enzymes which retain phytase activity.

By "phytase activity" is meant the liberation of inorganic phosphate or phosphorous from any of the various myo-inositol phosphates (mono-through hexa-phosphate).

Phytase activity may be determined by an enzyme activity assay as described in the prior art, e.g. WO 98/28408. More preferably, phytase activity is determined by the method of Heinonen and Lahti, *Anal. Biochem.* 113:313–317, 1981.

By "phytate" is meant the salt of myo-inositol hexaphosphoric acid.

According to one preferred embodiment of the invention, an isolated soybean phytase is characterized by a specific phytase activity of at least 50 mmol phosphate released/ minute/gram of protein. In this context, "specific activity" is the amount of phosphate liberated by one gram of protein from a solution of 0.0005 M dipotassium phytate at pH 4.5 in one minute. Specific details of such an assay are described in section 6.12, below.

According to another embodiment of the invention, an isolated polypeptide is provided which is encoded by a nucleotide sequence selected from the group consisting of:

(a) SEQ ID NO:1;

(b) a nucleotide sequence complementary to SEQ ID NO:1;

(c) a subsequence of SEQ ID NO:1 encoding a polypeptide having phytase activity;

(d) a nucleotide sequence capable of hybridizing under conditions of medium stringency with (a) or (b), or with a probe comprising at least 100 continuous nucleotides of (a) or (b); and (e) a homologous nucleotide sequence which is at least about 60% homologous with (a) or (b).

The invention also relates to an expression construct capable of directing the expression of a phytase in a suitable host cell. The expression construct comprises a nucleotide sequence encoding a soybean phytase operably linked to one or more control sequences compatible with the host cell. The control sequences are capable of directing the expression of peptides or proteins having phytase activity in the host cells. It should be understood that the expressed precursor protein may comprise an inactive or less active protein which is subsequently converted to a mature enzyme by post-translational modification, or other modification.

The invention also relates to vectors containing such an expression construct. The expression construct is inserted into a vector, preferably a plasmid, which is capable of transforming a host cell and integrating the expression construct into the host cell genome.

The invention further extends to a host cell transformed with a nucleotide sequence encoding a soybean phytase so that the host cell can express the phytase encoded by the nucleotide sequence.

The invention is directed to a method for producing a soybean phytase comprising:

transforming one or more host cells with a nucleotide sequence encoding a soybean phytase so that the host cell can express the phytase encoded by the nucleotide sequence; and growing a culture of the host cells under conditions conducive to the expression of the phytase by the host cells.

The invention also comprises transgenic plants transformed with a nucleotide sequence encoding a soybean phytase so that the phytase encoded by the nucleotide sequence can be expressed by the plant.

The invention extends to methods of producing such transformed plants. A method for producing a transgenic plant, comprises:

transforming a plant with a nucleotide sequence encoding a soybean phytase so that said plant can express said phytase; and growing said plant under conditions conducive to the expression of the phytase by the plant.

As used herein, "transgenic plant" includes not only whole transgenic plants, but also plant parts such as tissues, seeds, and cells. Preferably, the expression of soybean phytase in the plant is placed under the control of a seed-specific promoter.

The invention is also directed to a feed or food composition comprising such a transgenic plant. By "feed composition" and "food composition", respectively, means any natural or artificial diet, meal or the like, or components of such meals intended or suitable for being eaten, taken in, and digested by an animal or human, respectively. The terms "feed composition" and "food composition" are also intended to include preparations from transgenic plants useful as additives or supplements to feeds or foods.

The invention is also directed to feed or food additives comprising an isolated soybean phytase. A "feed or food additive" is a single component or multi-component preparation which contains at least the soybean phytase, and optionally other enzymes, vitamins, minerals or other substances useful as food processing aids or nutritional supplements, and optional carriers and/or excipients well-known to those skilled in the art. The additive preparation is combined with foods containing phytate in order to break down that substrate to promote phosphorous utilization.

The invention also comprises antibodies, and preparations thereof, produced by immunizing an animal with essentially pure soybean phytase or an immunogenic fragment thereof. Preferably, the antibodies are produced by immunization with essentially pure soybean phytase having the amino acid sequence SEQ ID NO: 2 or SEQ ID NO: 3. According to another embodiment, the antibody specifically binds with soybean phytase, or immunogenic fragment thereof.

By "specifically bind" as used to describe the interaction between an antibody and another molecule is meant that the two bind to each other with greater affinity than to other, non-specific molecules.

4. DESCRIPTION OF THE FIGURES

FIGS. 1(*a*), (*b*) and (*c*) illustrate the cloning of the full-length soybean phytase coding sequence. FIG. 1(*a*) shows a 5' genomic DNA PCR product containing KpnI and EcoRV sites blunt-end ligated into the SmaI site of plasmid pTZ19R. FIG. 1(*b*) shows the result of digestion of the FIG. 1(*a*) plasmid with EcoRV, followed by blunt-end ligation to the 3' PCR product of the soybean phytase cDNA 3' end amplification, which had been previously digested with EcoRV and SmaI. FIG. 1(*c*) shows the result of the excision of the full length soybean phytase coding sequence from the FIG. 1(*b*) plasmid with KpnI, followed by subcloning into the unique KpnI site of the transformation vector p35SD.

5. DETAILED DESCRIPTION OF THE INVENTION

5.1 Introduction

Figure 1A:
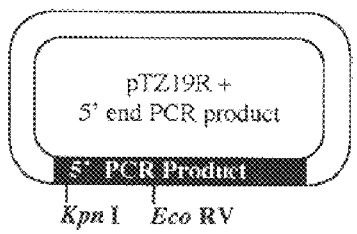

The gene for soybean phytase has been cloned and sequenced, and the nucleotide sequence of the gene is provided. The isolation of this polynucleotide permits the efficient production of soybean phytase on an industrial scale by modern recombinant DNA techniques.

Cloning of the soybean phytase gene enables, for the first time, the engineering of plant species with recombinant expression constructs using known plant transformation techniques in order to produce soybean phytase under the control of tissue-specific expression control elements. Isolation of the soybean phytase gene enables the transformation of soybean tissue cultures with appropriate vectors containing such constructs. In particular, expression of the soybean phytase gene under the control of a seed-specific promoter in a soybean host permits, for the first time, the pre-germination expression and accumulation of phytase in soybeans. The expressed phytase serves to reduce the phytate content of soybeans from transformed soybean plants, and thus provide for increased phosphorous availability in meal and other feed products prepared from the transformed soybeans.

5.2 Nucleotide Sequences

In one aspect, the present invention relates to isolated nucleic acid sequences which encode a soybean phytase. Soybean phytase cDNA was recovered by purifying soybean phytase from soybean cotyledons, and obtaining a partial amino acid sequence. Degenerate primers were designed based upon the partial amino acid sequences and used to generate cDNA sequences by RT-PCR from mRNA generated from post-germination soybean cotyledons. It was found that the full-length cDNA could not be obtained directly due to the presence of secondary structure in the soybean phytase mRNA. Hence, the complete cDNA sequence encoding soybean phytase was ultimately recovered only following amplification of genomic DNA, inverse PCR, 5' end amplification of the genomic DNA and 3' end amplification of the cDNA The 5' genomic DNA PCR product containing KpnI and EcoRV sites was blunt-end ligated in the SmaI site of plasmid pTZ19R (MBI Fermentas, Inc.). The resulting plasmid was digested with EcoRV and blunt-end ligated to the 3' PCR product of the cDNA 3' end amplification, which had been digested with EcoRV and SmaI. The full length soybean phytase coding sequence was excised using KpnI and was subcloned into the unique KpnI site of the transformation vector p35SD. The soybean phytase cDNA contains a 1644 bp open reading frame encoding a protein of 547 amino acids. Protein analysis software demonstrated that the encoded protein exhibited a molecular weight of 62 kDa and an isoelectric point of 5.3, similar to the weight and isoelectric point of the purified phytase enzyme (see below).

According to one embodiment of the invention, the nucleic acid sequence is the full-length soybean phytase cDNA as set forth as SEQ ID NO:1, which encodes the soybean phytase having the amino acid sequence SEQ ID NO:2. The amino acid sequence of SEQ ID NO:2 represents the soybean phytase precursor protein which is cleaved to form the mature soybean phytase enzyme having the amino acid sequence set forth as SEQ ID NO:3. The mature form differs from the precursor in the absence of the N-terminal signal sequence MASITFSLLQFHRAPILLLILLAGFGHC (SEQ ID NO:24) found in SEQ ID NO:2. The present invention also encompasses nucleic acid sequences which encode an amino acid sequence set forth in SEQ ID NO:2 or SEQ ID NO:3, which differ from SEQ ID NO:1 by virtue of the degeneracy of the genetic code. The present invention also relates to subsequences of SEQ ID NO:1 which encode a fragment of SEQ ID NO:3 which retains phytase activity.

Preferably, such subsequences contain at least 900, more preferably at least 1200, more preferably at least 1500 nucleotides.

In addition to the soybean phytase nucleotide sequence, the invention also encompasses complementary sequences and fragments thereof. These sequences include DNA and RNA, and analogues thereof, such as peptide nucleic acids.

The invention also relates to nucleic acid sequences which have a degree of homology of at least about 60%, more preferably at least about 70%, more preferably at least about 80%, even more preferably at least about 90%, still more preferably at least about 95%, and most preferably at least about 97%, with the nucleotide sequence set forth in SEQ ID NO:1. The degree of identity or "homology" between two nucleic acid sequences may be determined by means of computer programs known to those skilled in the art such as the GAP program provided in the GCG program package (Program Manual for the Wisconsin Package Version Aug. 8, 1996, Genetics Computer Group, 575 Science Drive, Madison, Wis. 53711) (Needleman and Wunsch, *J. Mol. Biol.* 48:443–453, 1970). GAP is used with the following settings for DNA sequence comparison: GAP creation penalty of 5.0 and GAP extension penalty of 0.3.

The invention also relates to polynucleotides which encode phytases, which polynucleotides are capable of hybridizing under conditions of low, medium or high stringency (i) to the polynucleotide of SEQ ID NO:1; (ii) to a probe comprising at least 100, more preferably at least 250, most preferably at least 500 continuous nucleotides of SEQ ID NO:1; or (iii) to the complementary strand of either SEQ ID NO:1 or the probe (J. Sambook et al., 1989 *Molecular Cloning, A Laboratory Manual*, 2nd edition, Cold Spring Harbor, N.Y.; Berger and Kimmel, "Guide to Molecular Cloning Techniques" *Methods in Enzymology*, vol. 152, Academic Press, 1987). For example, such hybridization conditions include prehybridization and hybridization at 42° C. in 5×SSPE, 1×–5× Denhardt's reagent, 0.3% SDS, 200 µg/ml sheared and denatured heterologous DNA such as salmon sperm DNA, and either 50, 35 or 25% formamide for high, medium and low stringencies, respectively, following standard Southern blotting procedures.

Homologous nucleic acid sequences, defined in terms of either degree of homology with or ability to hybridize to a reference nucleic acid sequence, may be derived which encode peptides which function the same or similar to soybean phytase. Using the sequence data provided herein, it is within the skill in the art to obtain nucleotide sequences other than SEQ ID NO:1 which encode phytases which are similar in function to the soybean phytase. Such modifications at the nucleic acid level include, for example, modification to the nucleotide sequence which are silent, which change the amino acids without structural or function effects on the encoded peptide, or which change the amino acids (substitutions, insertions or deletions) with structural or function effects on the encoded peptide, e.g., to improve activity, expression or secretion. Preferably, such changes do not adversely alter the enzymatic activity of the phytase. The present invention also relates to nucleotide changes which result in fusions and truncations of the enzyme, which preferably retain the same or similar activity to the enzyme encoded by the reference polynucleotide. Thus, the present invention relates to variants of the herein-described nucleotide sequences, which variants encode phytases which may be regarded as derivatives or analogues of the phytase precursor (SEQ ID NO:2) or mature enzyme (SEQ ID NO:3). It should be appreciated that the polynucleotide variant may be a naturally occurring allelic variant or a non-naturally occurring variant.

The isolated nucleic acid sequence of the invention may be in the form of DNA, inclusive of cDNA, genomic DNA, and synthetic DNA. The DNA may be double-stranded or single-stranded, and if single-stranded may comprise either the coding strand or non-coding (antisense) strand. The nucleotide sequence of the invention also extends to RNA, and nucleic acid analogues such as peptide nucleic acids.

The isolated nucleotide sequences of the invention embrace not only nucleic acid sequences such as SEQ ID NO:1 which encode the precursor soybean phytase enzyme (SEQ ID NO:2), but also nucleotide sequences which encodes the mature enzyme (the mature enzyme amino acid sequence being stated in SEQ ID NO:3). Also, as used herein, the term "nucleic acid sequence encoding" encompasses a nucleotide sequence which includes not only the coding sequence for the phytase enzyme, but may extend to additional sequences which are coding and/or noncoding. Thus, embraced by the present invention are nucleic acid sequences encoding for the mature enzyme wherein the coding sequence is fused in the same reading frame to a nucleic acid sequence which aids in expression and/or secretion of the enzyme in a host cell, for example a signal sequence, which functions to transport the enzyme from the cell. The enzyme having a signal sequence is a precursor and may have the signal sequence cleaved by the host cell to form the mature form of the enzyme. The isolated nucleotide sequences of the invention may also encode for polypeptides which comprise the mature protein plus additional 5' amino acid residues. Thus, the nucleotide sequences of the present invention may encode for a mature enzyme, or for a protein which is an active or inactive precursor of the mature enzyme.

The invention is also directed to nucleotide sequences which may be used to define probes which may be in turn utilized for hybridization screening studies for identifying phytases from other species, particularly plant phytate genes. Such probes may be labeled with any analytical detectable reagent to facilitate identification of the probe. The probe is preferably comprises at least 18, more preferably at least 25, most preferable at least 40, continuous nucleotides of SEQ ID NO:1, or complement thereof.

5.3 Amino Acid Sequences

The invention is also directed to an isolated soybean phytase comprising the amino acid sequence SEQ ID NO:2. or SEQ ID NO:3, or functional derivative thereof, or fragment of SEQ ID NO:3 having phytase activity.

Preferably, the isolated polypeptide has an amino acid sequence which is at least about 70%, more preferably at least about 80%, even more preferably at least about 85%, more preferably at least about 90%, and most preferably at least about 95% homologous to SEQ ID NO:2 or SEQ ID NO:3. "Homology" as applied to amino acid sequences is determined as the degree of identity between two sequences. Homology may be suitably determined by means of computer programs known in the art such as GAP provided in the GCG version 8 program package (Program Manual for the Wisconsin Package Version Aug. 8, 1996, Genetics Computer Group, 575 Science Drive, Madison, Wis. 53711) (Needleman and Wunsch, *J. Mol. Biol.* 48:443–453, 1970). GAP is used with the following settings for polypeptide sequence comparison: GAP creation penalty of 5.0 and GAP extension penalty of 0.3. In a preferred embodiment of the invention, the homologous polypeptides have an amino acid sequence which differs from SEQ ID NO:2 or SEQ ID NO:3 by 5, 4, 3, 2 or 1 amino acid(s).

A functional derivative or homologous amino acid sequence can differ from the reference amino acid sequence of SEQ ID NO:2 or SEQ ID NO:3 by the insertion, deletion or addition of one or more amino acid residues. Preferably, amino acid changes are of a minor nature, and comprise conservative amino acid substitutions, that do not significantly affect the folding and/or other activity of the protein; small deletions, typically of no more than about 30 amino acids, small amino- or carboxy-terminal additions such as addition of an amino-terminal methionine residue, small linkers of up to 25 amino acids, or small extensions which facilitate purification by changing the net charge or other characteristic, e.g., a poly-histidine binding tract.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, e.g., by H. Neurath and R. L. Hill, 1979, *In the Proteins*, Academic Press, New York.

In a preferred embodiment, the present invention relates to isolated polypeptides having phytase activity which comprise the amino acid sequence set forth in SEQ ID NO: 3, and allelicforms and fragments thereof which retain phytase activity. Preferably, a fragment contains at least 100 amino acid residues, more preferably at least 250 amino acid residues, and most preferably at least 500 amino acid residues.

Also included in the scope of the present inventions are glycosylated as well as nonglycosylated polypeptides. The soybean phytase which has been isolated to a high degree of purity by the isolation procedure detailed herein is believed to be glycosylated. The phytase-degrading protein has been isolated through a multi-step process (ammonium sulfate fractionation, heat denaturation of contaminating proteins, cation exchange chromatography, lectin affinity chromatography, met al chelate affinity chromatography, high resolution anion exchange chromatography—see protocols below). Based on separation on a gel filtration column and filtration over a Centricon membrane with a molecular weight cut off of 100,000 daltons, it is believed that the protein in its native form is at least a dimer. Based on polyacrylamide gel electrophoresis, the size estimate for the phytase monomer is 60–75 kD. Evidence that the isolated soybean phytase protein is glycosylated includes: 1) purification protocol that includes a affinity chromatography step over a lectin affinity column (conA), 2) periodic acid Schiff staining of the phytase band on a gel, and 3) a difference between the observed migration of the protein band at approximately 60–75 kD on a polyacrylamide gel and a predicted molecular mass of 59.1 kD from the cDNA sequence encoding the mature protein (lacking the signal sequence). Recombinant expression of this glycosylated form will require a eukaryotic host, such as yeast or plant cells, to achieve glycosylation of the protein.

The invention is also directed to feed or food additives comprising soybean phytase which is at least partially purified. A feed or food additive is a single component or multi-component preparation which contains at least the soybean phytase, and optionally other enzymes, vitamins, minerals or other substances useful as food processing aids or nutritional supplements, and optional carriers and/or excipients well-known to those skilled in the art. The additive preparation is combined with foods containing phytate in order to break down that substrate to promote phosphorous utilization.

5.4 Recombinant Expression of Soybean Phytase DNA

The polynucleotides described herein may be used to produce recombinant phytase polypeptides. The resulting polypeptides may be used as functional phytases, such as in supplementing animal feeds or human foods, or the polypeptides may be expressed in vivo, as in plants.

To produce the phytase polypeptide, the appropriate polynucleotide is inserted into a suitable expression vector for expressing an enzyme. By "vector" is meant any means for the transfer of a nucleic acid into a host cell. A recombinant molecule is constructed in which cDNA encoding soybean phytase is operably linked to a heterologous expression control sequence permitting expression of the phytase amino acid sequence. By "operably linked" is meant that a polypeptide coding region is connected to a regulatory element in such a way that the regulatory element can permit expression of the polypeptide when appropriate molecules (such as activator proteins and polymerases) are present in a cell or cell free system.

Such vectors may include, for example, chromosomal, non-chromosomal, and synthetic DNA sequences; bacterial plasmids; phage DNA; baculovirus; yeast plasmids; and the like. Any vector may be utilized so long as it is replicable and viable in the host. Examples of prokaryotic vectors include the pBluescript vector series (Stratagene), the pQE vector series (Qiagen), and the pET vector series (Novagen). Specific examples include, but are not limited to: pQE70, pQE60 and pQE-9 (Qiagen); pBluescript II (Stratagene); pTRC99a, pKK223-3, and pRIT2T (Pharmacia). Specific examples of eukaryotic vectors include, but are not limited to, plant vectors such as pBI101, pBI101.2, pBI101.3, pBI121 and pBI221 (all commercially available from Clontech Laboratories, Palo Alto, Calif.). Except for pBI221, the aforementioned Clontech vectors are binary vectors suitable for gene gun applications. Each vector contains a β-glucuronidase (GUS) sequence which may be removed prior to the use of the vector. Further vectors include pBIB-KAN and pBIB-HYG (Becker, *Nucleic Acids Res.* 1990. 18(1)). It should be appreciated, however, that expression in prokaryotic hosts will give rise to nonglycosylated polypeptides. Expression of glycosylated soybean phytase molecules may be achieved only in eucaryotic hosts, preferably plant hosts. For expression of glycosylated polypeptides, the vector should therefore be selected accordingly.

The DNA sequence encoding the phytase in the expression vector is operably linked to an appropriate expression control sequence(s), to direct mRNA synthesis. By "control sequences" is meant any of the components which are necessary or advantageous for expression of the coding sequence of a nucleotide sequence. Each control sequence may be native or foreign to the nucleic acid sequence encoding the polypeptide. Control sequences include, but are not limited to, a leader, a polyadenylation sequence, a promoter, a signal sequence, and a transcription terminator. The control sequences may be provided with linkers for the purpose of introducing specific restriction sites facilitating ligation of the control sequences wit the coding region of the nucleic acid sequence encoding the polypeptide.

The promoter may be any DNA sequence which is transcriptionally active in the host cell. Promoters that may be used in the present invention include both constitutive promoters and regulated (inducible) promoters. The promoter may be derived from genes encoding proteins which are either homologous or heterologous to the host cell. Procedures for ligating the DNA sequences coding for the phytase, the promoter, the terminator and any other control sequences which may be present, and procedures for inserting these sequences into suitable vectors, are well-known to those skilled in the art. See, e.g., Sambrook (*Molecular Cloning*, Cold Spring Harbor Laboratories, Second Ed., 1989), and in Ausubel (*Current Protocols in Molecular Biology*, Wiley and Sons, 1987), which are incorporated by reference. Restriction enzyme digestion and ligation are the basic steps employed to join two DNA fragments. The ends of the DNA may require modification prior to ligation. This may be accomplished by filling in overhangs, deleting terminal portions of the fragments with nucleases, site directed mutagenesis, and adding new base pairs by polymerase chain reaction. Polylinkers and adaptors may be employed to facilitate joining of fragments.

Such promoters include, for example, Cauliflower Mosaic Virus 35S promoter, *E. coli lac* or trp, phage lambda $P_L$ promoter and other promoters known to control expression of genes in prokaryotic or eukaryotic cells or their viruses. Among the eukaryotic (including viral) promoters useful for practice of this invention are ubiquitous promoters (e.g., actin and tubulin), tissue-specific and developmentally-regulated promoters such as the seed-specific soybean β-conglycinin α' promoter (Chen et al., *Proc. Nat. Acad. Sci. USA* 83: 8560–8564, 1986), and tetracycline-regulated transcriptional modulators. For a discussion of tetracycline-regulated and other chemically regulated promoters for transgenic plants see Gatz, *Current Opinion in Biotechnology* 7:168–172 (1996), incorporated herein by reference. Examples of polyadenylation signals that can be used in the present invention in plant hosts include but are not limited to the polyadenylation signal of the nopaline synthase (NOS) gene of the Agrobacterium tumor-inducing (Ti) plasmid or the β-conglycinin storage protein gene.

The expression vector also contains a ribosome binding site for translation initiation and a transcription terminator. The vector may also include appropriate sequences for amplifying expression and one or more selectable marker genes to provide a phenotypic trait for selection of transformed host cell. Such traits include, for example, gentamycin, kanamycin, hygromycin and herbicide resistance for plant host cells, and tetracycline or ampicillin resistance for *E. coli* host cells.

The expression vector is introduced into host cells by any number of gene transfer techniques such as natural competence, chemically mediated transformation, protoplast transformation, electroporation, biolistic transformation, transfection, or conjugation, for example. The gene transfer system selected depends on the nature of the host cells and vector used.

Examples of hosts include bacterial cells such as *E. coli*, Streptomyces, *Bacillus subtilis*; fungal cells such as yeast; insect cells such as Drosophila S2 and Spodoptera Sf19; animal cells such as CHO or COS; and plant cells. Eukaryotic are preferred as the soybean phytase is believed to exist in glycosylated form.

Following transformation of a suitable host strain and growth of the host strain to an appropriate cell density, the selected promoter is induced by appropriate means (e.g., chemical induction or temperature shift) and cells are cultured for an additional period. The cells are harvested by centrifugation or other means, disrupted by physical or chemical means, and the resulting crude extract retained for further purification.

The enzyme may be recovered and purified from the recombinant cell cultures by a combination of procedures including protein extraction with ammonium sulfate, centrifugation, cation exchange chromatography, lectin affinity chromatography (for glycosylated forms), met al chelate affinity chromatography and high resolution anion exchange chromatography. A complete purification protocol is contained in Example 1, below. The purified polypeptide may be partially or completely sequenced and compared to SEQ ID NO:2 (precursor) or SEQ ID NO:3 (mature enzyme) to verify that the correct molecule has been purified.

5.5 Expression of Soybean Phytase DNA in Plants

According to a preferred embodiment of the invention, the soybean phytase gene is expressed in a plant host to induce or enhance phytase expression in one or more parts of the plant. The resulting transgenic plants may be dicotyledonous or monocotyledonous. Of particular interest are plants which are potential food or feed components and which comprise phytate. Dicots are particularly preferred, most preferably soybean. It should be noted that the term "transgenic plant" includes not only the initial generation of plants from tissue culture containing the transgene, but also transgenic progeny of such transgenic plants.

According to one such embodiment of the invention, the soybean phytase gene is expressed in plant hosts to achieve specific, targeted expression in plant seeds in order to lower the phytate content of the seeds. Accordingly, hosts for expression of the soybean phytase DNA in this embodiment would be any plant that is harvested for its seed or grain. Alternatively, the soybean phytase may be expressed to achieve possible over-expression of the plant phytase in other parts of the plant used for feed or food purposes. A much broader range of plant hosts is thereby implicated. Hosts include, for example, Arabidopsis, alfalfa, cauliflowers, artichokes, apples, bananas, cherries, cucumbers, grapes, lemons, melons, nuts, oranges, peaches, pears, endives, leeks, lettuce, spinach, tobacco, beets, carrots, cassava, turnips, radishes, yams, sweet potato, beans, peas, soy beans, wheat, barley, corn, rice, rapeseed, millet, sunflower, oats, tubers, potatoes and the like. Introduction of phytase expression to lower phytate in the seeds requires that the expressed protein be localized to the site of phytate accumulation during seed development. Expression as a source of phytase generally in the plant would not require targeting of the protein to the site of phytase accumulation.

Expression in plant hosts is obtained by means of an expression construct containing at least: the DNA encoding the soybean phytase; sequences encoding a selectable marker for recovery of transformants (such as hygromycin, or herbicide resistance marker); a promoter sequence forconstitutive, growth stage-specific, ororgan-specificexpression, e.g., the constitutive dual-enhanced Cauliflower Mosaic Virus 35S promoter (Carrington and Freed, *J. Virol.* 64:1590–1597, 1990; Fang et al., *Plant Cell* 1:141–150, 1989; Kay et al., *Science* 236: 1299–1302,1987), orthe soybean seed specific promoter from the soybean β-conglycinin a' promoter (Chen et al., *Proc. Nat. Acad. Sci. USA* 83: 8560–8564, 1986); and a transcription terminator/polyadenylation signal. Targeting sequences and secretory sequences may be included. The sequences are assembled and joined by the conventional ligation techniques discussed above. The various regulatory elements may be homologous (native) to the plant or they may be heterologous.

Methods for producing stable transgenic plants are known to those skilled in the art. See, e.g., EP 449,375 (1991), incorporated herein by reference.

One method for production of transgenic plants expressing heterologous phytase genes (in this case phytase genes from the fungal genus Aspergillus), is described in U.S. Pat. No. 5,824,779, the entire disclosure of which is incorporated by reference. This so-called "binary" method utilizes a strain of Agrobacterium containing a modified Ti plasmid (which includes genes for virulence) and a second, compatible plasmid (which includes the gene construct to be translocated). Briefly, double-strand cDNA encoding the desired protein is linked with plant regulatory sequences. The construct is then sub-cloned into a binary vector such as PBIB-KAN or PBIB-HYG (Becker, *Nucleic Acids Res.* 1990. 18(1)). The vector is then introduced into *Agrobacterium tumefaciens* containing a disarmed Ti plasmid. This can be done by any number of well known means, such as by electroporation. Bacterial cells containing the construct are co-cultivated with tissues from the plant to be transformed, and transformed plant cells are selected using nutrient media containing antibiotics. The transformed cells are induced to differentiate into plants on suitable nutrient media. The plants so produced will produce seeds which contain and express the gene construct.

To produce plants which constitutively express the phytase gene construct, the phytase-encoding gene construct is placed under the regulatory control of the dual-enhanced CMV 35S promoter. The construct is then subcloned into a binary vector as described above. The vector is then introduced into *Agrobacterium tumefaciens* containing a disarmed Ti plasmid. Bacterial cells containing the construct are co-cultivated with tissues from the plant to be transformed, and transformed plant cells are selected using nutrient media containing antibiotics. The transformed cells are induced to differentiate into plants on suitable nutrient media. The plants so produced constitutively express active phytase.

A more detailed protocol, illustrating the production of transgenic alfalfa expressing fungal phytase, is set forth in U.S. Pat. No. 5,824,779, the entire disclosure of which is incorporated herein by reference. The transformation method of U.S. Pat. No. 5,824,779 is an *Agrobacterium tumefaciens*-mediated transformation method.

A method for transformation of soybean explants and regeneration of the transformed explant into a differentiated transformed plant is described in U.S. Pat. No. 5,824,877, the entire disclosure of which is incorporated herein by reference. The method may be used to introduce foreign genes into soybeans. The transformation method of U.S. Pat. No. 5,824,877 is an *Agrobacterium tumefaciens*-mediated transformation method.

Preferably, the host for transformation comprises soybean plants. Procedures for soybean transformation are well-established in the literature, including so-called "gene gun" (Finer et al., *Plant Cell Rep.* 11:
323–328, 1992; Bond et al., *Tenn. Farm Home Sci.* 162:4–14, 1992; Vain et al., *Plant Cell, Tissue and Organ Cult.* 33:237–246, 1993) and *Agrobacterium tumefaciens*-mediated transformation. The *Agrobacterium tumefaciens*-mediated transformation method described in U.S. Pat. No. 5,824,877 may be applied directly to soybean plants. Preferred vectors for plant transformation include plasmids suitable for either the gene gun bombardment method or the

*Agrobacterium tumefaciens* method. In either case, the vector preferably contains the CaMV 35S or seed specific promoter. The protocols for preparing such vectors involve the insertion of the soybean phytase cDNA into the vectors along with the necessary selectable markers and transcription signals, as well as T-DNA border sequences for the Agrobacterium vectors.

According to one preferred embodiment of the invention, a transformation vector designated p35SD, useful in the gene gun method of transformation, was derived from the plasmid construct pPHY35P of Li et al. *Plant Physiol.* 114:1103–1111, 1997, the entire disclosure of which is incorporated herein by reference. The construct was formerly utilized by Li et al. to obtain expression of a fungal phytase in soybean cell-suspension cultures. To prepare p35SD, a DNA fragment containing a KpnI site was inserted at the 3' end of the fungal phytase coding sequence in construct pPHY35P, allowing for removal of the fungal sequence by KpnI digestion. The p35SD vector was generated by intramolecular ligation of the KpnI ends. The full-length soybean phytase coding sequence was excised from plasmid pTZ19R containing the coding sequence (from Example 2, below,) using KpnI and was subcloned into the unique KpnI site of plasmid p35SD (FIG. 1c).

According to another embodiment of the invention, a transformation vector designated pSSP, useful in the gene gun method of transformation, is derived from the plasmid construct pPHYSSPss (Li et al., *Plant Physiol.* 114:1103–1111, 1997). Plasmid pPHYSSPss contains the fungal phytase gene. SalI sites flanking the 5' and 3' ends of the fungal gene allow for removal of the fungal sequence and subsequent intramolecular ligation. The pSSP vector is linearized by digestion with SalI and the resulting ends are converted to blunt termini using T4 DNA polymerase. The full-length soybean phytase coding sequence is excised from pTZ19R using KpnI, treated with T4 DNA polymerase to obtain blunt termini, and blunt-end ligated into the prepared pSSP vector.

Binary transformation vectors have been previously generated by inserting the dual-enhanced CaMV 35S promoter as a HindIII-KpnI fragment into PBIB-KAN or pBIB-HYG (Becker, *Nucleic Acids Res.* 1990. 18(1), incorporated herein by reference). The full-length soybean phytase coding sequence may be excised from pTZ19R using KpnI and then subcloned into the unique KpnI site in the appropriate binary vector.

Transformation of soybean cultures with a vector including a seed-specific promoter, such as the soybean β-conglycinin α' promoter, gives rise to soybean plants which express phytase in their seeds during seed development, in advance of germination. Phytase expression during seed development results in accumulation of the enzyme in the soybean, and reduction of phytate. When converted into meal, this engineered soybean provides an animal feed containing phosphorous in a form which may be readily utilized by non-ruminant animals, thereby reducing dependence on expensive feed supplementation to include inorganic phosphorous or commercial phytase preparations. Phytate utilization also serves to resolve environmental concerns attendant with phytate excretion into the environment.

For quantitative measurement of phytase activity, release of inorganic phosphate from phytate may be measured by the method of Heinonen and Lahti, *Anal. Biochem.* 113:313–317 (1981), as applied in Example 1 hereto. The efficacy of phytase in transgenic soybeans may be evaluated using an in vitro assay with soybean meal (Zyla et al., *Poultry Sci.* 72:72, 1993, incorporated herein by reference). The procedure is designed to expose a sample to conditions similar to those found in the gastrointestinal tract of chickens as feed passes through the crop, gizzard and small intestine, respectively.

Other methods for expressing phytase genes in plants are described in U.S. Pat. No. 5,593,963 to van Ooijen et al., the entire disclosure of which is incorporated herein by reference.

The harvested transgenic plants expressing the soybean phytase, inclusive of transgenic isolated plant parts, e.g., seeds, may be used to prepare feed or food compositions. In particular, soybeans from transgenic soybean plants transformed to achieve seed-specific phytase expression may be processed to produce soy products, particularly soy meal, which contains reduced phytate content due to the expression of phytase. Moreover, such products may be utilized as a phytase additive or supplement for animal or nutrition. The addition of soybean phytase sources to feeds or foods serves to break down phytate in such materials, thereby promoting phosphorous utilization.

5.6 Probes for Soybean Phytase Gene Expression

Based upon the nucleotide sequence of the soybean phytase gene provided herein, nucleic acid probes may be prepared for identifying expression of the gene in samples of interest. For example, a nucleic acid library such as a cDNA library may be screened with such a probe. A DNA or RNA probe, based upon SEQ ID NO:1, which specifically hybridizes to complementary soybean phytase DNA or RNA, may be used to identify soybean phytase gene expression according to conventional hybridization probing techniques. Alternatively, the probe may be designed based upon an amino acid sequence contained within SEQ ID NO:2. The probes will contain, e.g. at least 12, more preferably at least 15, nucleotides. Probes may be generated according to methods known in the art, such as PCR. Primers may be designed based upon phytase-conserved sequences; the resulting PCR product is used as a probe to screen a nucleic acid library, such as a cDNA library.

5.7 Production of Anti-Soybean Phytase Antibodies

The soybean phytase protein, as well as modified version, fragments or analogs thereof, are useful as immunogens for the development of antibodies to soybean phytase. Either the ultra-purified soybean phytase recovered through the purification procedure disclosed herein, or the recombinant soybean phytase provided herein, may be used to generate antibodies specific for soybean phytase.

Useful antibodies include monoclonal, chimeric and single chain antibodies, as well as fragment of antibodies such as Fab, Fab', (Fab')$_2$, Fv and SCA fragments, or the production of an Fab expression library. Antibodies may be produced by conventional methods known to the art.

Antibodies generated against the soybean phytase enzyme can be obtained by direct injection of immunogen into an animal, preferably a nonhuman. The immunogen may comprise intact soybean phytase or an immunogenic fragment thereof. Fragments may be obtained by digesting purified or recombinant soybean phytase, or by recombinant expression of DNA encoding such fragments. Identification of fragments which are immunogenic in the host animal may be easily determined by those skilled in the art. The antibody so obtained will then bind the soybean phytase itself. In this manner, even a sequence encoding only a fragment of the soybean phytase can be used to generate antibodies binding the whole native enzyme. Such antibodies can then be used to isolate soybean phytase from cells expressing that enzyme.

For preparation of monoclonal antibodies, any technique which provides antibodies produced by continuous cell line cultures can be used. Examples include the hybridoma technique (Kohler and Milstein, 1975, *Nature*, 256:495–497), the trioma technique, the human B-cell hybridoma technique (Kozbor et al. 1983, *Immunology Today*, 4:72), and the EBV-hybridoma technique to produce human monoclonal antibodies (Cole, et al., 1985, in Monoclonal Antibodies and CancerTherapy, Alan R. Liss, Inc., pp. 77–96).

Techniques described for the production of single chain antibodies (U.S. Pat. No. 4,946,778) can be adapted to produce single chain antibodies to immunogenic products of this invention. Also, transgenic mice may be used to express humanized antibodies to immunogenic enzyme products of this invention.

Antibodies generated against soybean phytase may be used in screening for similar enzymes from other organisms and samples. Such screening techniques are known in the art. Antibodies may also be employed as a probe to screen gene libraries generated from this or other organisms to identify this or cross reactive activities.

Isolation and purification of polypeptides produced in the systems described above can be carried out using conventional methods, appropriate for the particular system. For example, preparative chromatography and immunological separations employing antibodies, such as monoclonal or polyclonal antibodies, can be used.

The term "antibody," as used herein, refers to intact immunoglobin molecules, as well as fragments of immunoglobulin molecules, such as Fab, Fab', (Fab')$_2$, Fv, and SCA fragments, that are capable of binding to an epitope of an the phytase polypeptide. These antibody fragments, which retain some ability to selectively bind to the antigen of the antibody from which they are derived, can be made using well known methods in the art. Such methods are generally described in U.S. Pat. No. 5,876,997.

The polypeptide or peptide used to immunize an animal can be obtained by standard recombinant, chemical synthetic, or purification methods. It may be glycosylated or nonglycosylated. For example, the full-length soybean phytase coding sequence may be excised from pTZ19R using KpnI and subcloned into the unique KpnI site of the expression vector pET-32a(+) (Novagen). The plasmid may then be introduced into the bacterial host strain BLR(DE3) pLysS (Novagen). The expressed recombinant protein is purified by met al affinity chromatography and used as an immunogen to generate antibody against soybean phytase.

According to one embodiment of the invention, antibodies against soybean phytase are generated in chickens. After recovery of the phytase polypeptide by affinity chromatography, it is used to immunize chickens. Immunization of chickens is similar to that of rabbits with respect to route of injection, amount of antigen used and the kinetics of specific antibody generation (Promega Protocols and Applications Guide). Laying hens are injected subcutaneously at multiple sites in the breast with 20–500 μg of antigen in complete Freund's adjuvant. Specific antibody titers are boosted by two to three additional weekly injections.

Egg yolks from immunized chickens are an excellent source of polyclonal antibodies, with several advantages over mammalian antibody production systems. A single egg contains as much antibody as an average bleed from an immunized rabbit, the sample procurement is non-invasive, and eggs are available on a daily basis. Purification of yolk immunoglobulin Y (IgY) is simple (EGGstract IgY Purification System from Promega) and chicken IgY does not cross-react with mammalian IgG, reducing non-specific binding. Eggs may be stored up to a year at 4° C. prior to IgY purification and yield 90–100 mg of total IgY. The specific antibody generally comprises 1–10% of the total, or 1–10 mg per egg.

As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

Phytase-specific polyclonal and monoclonal antibodies can be purified, for example, by binding to, and elution from, a matrix containing a phytase polypeptide, e.g., the phytase polypeptide (or fragment thereof) to which the antibodies were raised. Additional methods for antibody purification and concentration are well known in the art and can be practiced with the phytase-specific antibodies of the invention (see, for example, Coligan, et al., Unit 9, *Current Protocols in Immunology*; Wiley Interscience, 1994).

The antibodies raised against soybean phytase may be used for screening samples for the presence of the enzyme, according to conventional techniques. For example, the antibodies may be directly or indirectly labeled with a detectable label. The label may advantageously comprise, for example, a radionuclide in the case of a radioimmunoassay; a fluorescent moiety in the case of an immunofluorescence assay; a chemiluminescent moiety in the case of a chemiluminescent assay; and an enzyme which cleaves a chromogenic or fluorogenic substrate, in the case of an enzyme-linked immunosorbent assay.

The antibodies may also be immobilized to an appropriate solid support to carry out affinity immunopurification of soybean phytase from crude mixtures containing the enzyme. Methods for linking antibodies to solid supports, and the use of the anchored antibody for immunopurification of the corresponding antigen, are well-known to those skilled in the art.

6. EXAMPLES

The practice of the invention is illustrated by the following non-limiting examples.

6.1 Example 1

Purification and Partial Sequencing of Soybean Phytase Enzyme

The following enzyme purification procedure results in a highly purified (20,000–25,000 fold) preparation of soybean phytase.

6.11 Plant Material

Soybeans (*Glycine max* [L.] Merr. cv. Williams 82) were surface sterilized in 10% bleach for 20 minutes, washed with sterile $H_2O$, treated with 70% ethanol for 30 seconds, and rinsed thoroughly with sterile $H_2O$. After overnight imbibition in sterile $H_2O$, the seeds were placed on eight layers of damp paper towels in glass 9"×11" Pyrex baking dishes. The dishes were sealed with plastic wrap to retain moisture. Seeds were germinated in the dark for 10 to 11 days and water was added as needed. Seed coats, leaves and embryos were separated from the cotyledons and discarded. Cotyledons were rinsed in sterile $H_2O$ and blotted dry with a paper towel prior to storage at $-80°$ C.

6.12 Phytase Activity Assay

Crude extracts were assayed for phytase activity by the method of Heinonen and Lahti, *Anal. Biochem.* 113: 313–317 (1981). Samples were assayed at 55° C. in 50 mM NaOAc, pH 4.5 using 0.5 mM phytate (dipotassium salt) as the substrate. The reaction was carried out in a 500 µl reaction volume for 30 minutes. After incubation, 1.0 ml freshly prepared AAM solution (50% v/v acetone, 2.5 mM ammonium molybdate, 1.25 N sulfuric acid) was added to the reaction mixture. Absorbance was read at 355 nm in a spectrophotometer to quantify the release of inorganic phosphate from phytate. When assaying pure protein, 0.1 µg/µl of bovine serum albumin was added to the preparation to stabilize the enzyme.

6.13 Protein Extraction and Bulk Precipitation

Cotyledons (250 g) were homogenized in a kitchen blender (Oster) in 750 mL ice-cold extraction buffer (100 mM NaOAc, pH 5.5, 20 mM $CaCl_2$, 1 mM dithiothreitol, 1 mM phenylmethylsulfonyl fluoride). The process was repeated eight times to extract a total of 2 kg cotyledons in 6 L buffer. The crude extract was centrifuged at 4° C. in a Sorvall RC-5B using a GSA fixed-angle rotor at 10,000×g for 30 minutes. The resulting supernatant was incubated at 60° C. for 30 minutes as an initial heat-shock step to denature and precipitate contaminating proteins. The supernatant was then chilled on ice for 10 minutes and centrifuged (10,000×g, 20 minutes, 4° C., GSA fixed-angle rotor). The supernatant was taken to 50% saturation with solid ammonium sulfate and was stirred on ice for 30 minutes. After centrifugation (10,000×g, 20 minutes, 4° C., GSA fixed-angle rotor), the supernatant was recovered and increased to 80% ammonium sulfate saturation. The supernatant was stirred on ice and centrifuged as described above. The pellets were resuspended in a total volume of 100 mL buffer (50 mM NaOAc, pH 4.3) and dialyzed overnight against the same buffer (16 L). Any precipitate formed during dialysis was removed by centrifugation (10,000×g, 20 minutes, 4° C., SA-600 fixed-angle rotor) and vacuum filtration through a 1.2 µM membrane in a 115 mL disposable filtration unit (Nalgene).

6.14 Cation Exchange Chromatography

The cleared extract was applied to a CM-Sepharose cation exchange column (Pharmacia) equilibrated with cation buffer (50 mM NaOAc, pH 4.3). The column was washed extensively with cation buffer until the $A_{280}$ approached zero. Bound protein was eluted with a linear gradient of 30 to 30 285 mM NaCl in cation buffer. Fractions were collected and assayed for phytase activity. Active fractions were pooled and concentrated to 2.5 mL using Centriplus spin-concentrator units (50,000 MWCO, Millipore).

6.15 Lectin Affinity Chromatography

Concentrated con A affinity buffer (5×) was added to the sample to final concentration of 1× (100 mM NaOAc, pH 5.6, 500 mM NaCl, 1 mM $MgCl_2$, 1 mM $MnCl_2$, 1 mM $CaCl_2$). The sample was loaded onto a concanavalin A Sepharose column equilibrated with con A affinity buffer and washed extensively to remove unbound protein. Bound glycoproteins were eluted with 500 mM α-L-methylglucopyranoside in con A affinity buffer. The protein peak was collected and assayed for phytase activity. The active eluent was concentrated to 0.6 mL in MC buffer A (50 mM NaOAc, pH 5.5, 0.5 M NaCl) using a Centricon spin-concentrator (50,000 MWCO, Millipore).

6.16 Met al Chelate Affinity Chromatography

The phytase-containing fraction was loaded onto a iminodiacetic acid met al chelate column charged with $Cu^{++}$ ions and equilibrated with MC buffer A. The column was washed extensively then eluted in MC buffer A combined with a linear gradient of 0–100% MC buffer B (50 mM NaOAc, pH 4.0, 0.5 M NaCl). The resulting pH gradient ranged from pH 5.5 to pH 4.0. Collected fractions (3 mL) were assayed for phytase activity. Active fractions were pooled and concentrated to 0.4 mL in anion buffer (20 mM Tris-Acetate, pH 7.4) using a Centricon spin-concentrator (50,000 MWCO, Millipore).

6.17 High Resolution Anion Exchange Chromatography

The concentrated phytase-containing fractions from the met al chelate column were loaded onto a mono-Q high resolution anion exchange column (Pharmacia) equilibrated with anion buffer. The column was washed extensively with anion buffer (20 mM Tris-Acetate, pH 7.4) until the $A_{220}$ approached zero. Bound protein was eluted with a linear gradient of 105–285 mM NaCl in anion buffer. Fractions (1 mL) were collected and assayed for phytase activity. Active fractions were subjected to polyacrylamide gel electrophoresis. The fraction exhibiting the highest specific activity was concentrated using a Centricon spin-concentrator (50,000 MWCO, Millipore). Protein concentration was determined to be 0.625 µg/µL using the Protein Dot-Metric kit (GenoTech). An aliquot of the sample (150 µL) was used for sequence analysis.

Figure 4:
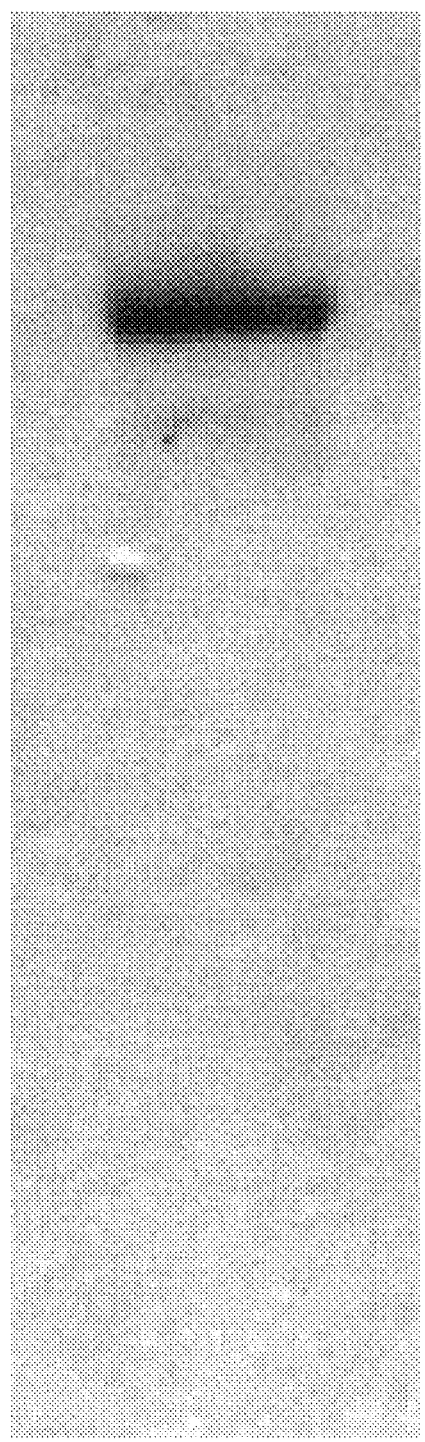
FIG. 4 is a Coomasie Blue-stained SDS-PAGE of a one microgram sample of purified soybean phytase of the present invention.

One microgram of the fraction was subjected to further SDS-PAGE and stained with Coomasie Blue. The result is shown in FIG. 4. The material appears to be essentially pure soybean phytase.

6.18 Determination of Optimum Activity pH

Figure 3:
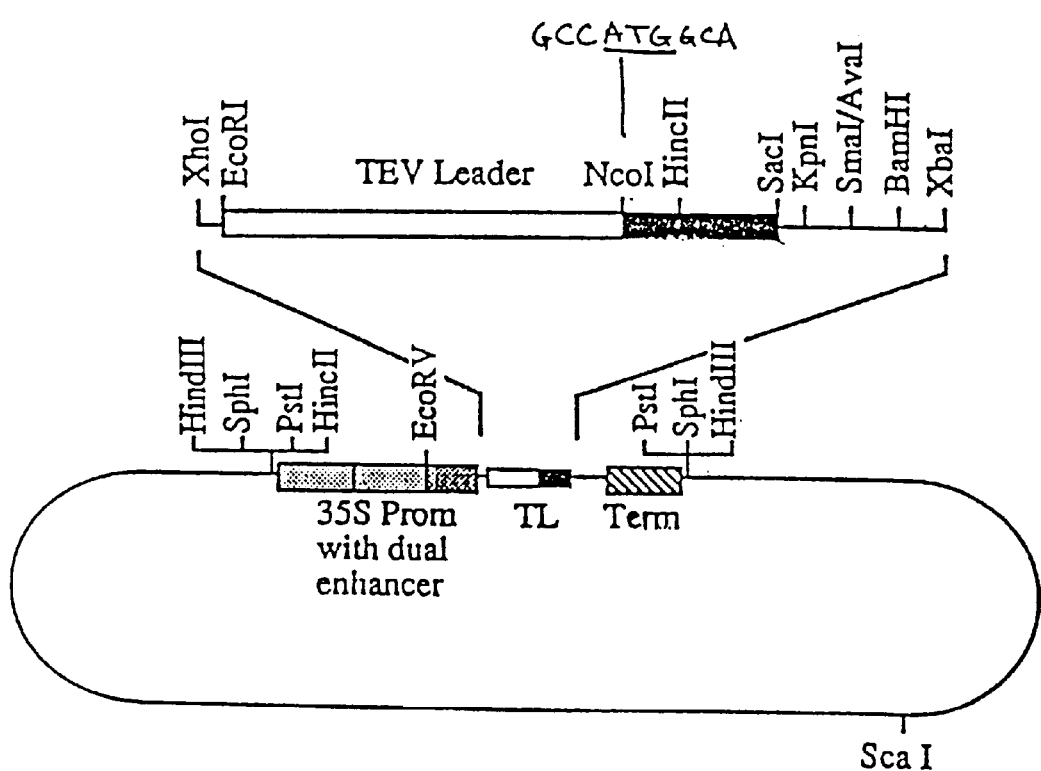
FIG. 3 is a restriction map of the plasmid pRTL-2, which contains the dual enhanced Cauliflower Mosaic Virus 35S promoter.

The activity of the purified enzyme was determined as a function of pH overthe range pH 2.0 to 7.0 as follows. Samples were assayed at 55° C. in 50 mM buffer (glycine buffer for pH 2.0, 2.5, and 3.0, acetate buffer for pH 3.5, 4.0, 4.5, 5.5, MES buffer for pH 6.0, 6.5, 7.0) using 1 mM phytate (dipotassium salt) as the substrate. The reaction was carried out in a 500 µl reaction volume for 30 minutes. After incubation, 1.0 ml freshly prepared AAM solution (50% v/v acetone, 2.5 mM ammonium molybdate, 1.25 N sulfuric acid) was added to the reaction mixture. Absorbance was read at 355 nm in a spectrophotometer to quantify the release of inorganic phosphate from phytate. The results are shown in FIG. 3. Soybean phytase is characterized by a single activity maximum at pH 4.5–5.0.

6.19 Amino Acid Sequencing

6.191 Sample Preparation

A portion of the sample (20 µg) was combined with 50 µL buffer (8M urea, 0.32 M Tris [pH 8], 80 mM methylamine hydrochloride) and was concentrated to approximately 50 µL in a vacuum centrifuge. The sample was incubated for 1 hour at 55° C. with 0.064% 2-mercaptoethanol to reduce disulfide bonds. The cysteine residues of the protein were alkylated by treatment with N-isopropyliodoacetamide. The protein was digested overnight at 370° C. with 0.5 µg lysyl peptidase. The reaction was stopped by adding trifluroacetic acid to a final concentration of 2% (v/v). The resulting peptides were separated on a Jupiter C18 column via HPLC. Fractions were collected and stored at −700° C. To ensure purity of peptides prior to sequencing, several fractions were subjected to further chromatography using a Vydac C18 column. The peptide fractions selected for sequencing eluted at 49.745 minutes and 34.466 minutes from the original run, 56.856 minutes from the rerun of fraction 46.741, and 51.296 minutes from the rerun of fraction 43.581.

6.192 Edman degradation

For determination of the N-terminal sequence of the undigested phytase protein, an estimated 50 pmole of protein was absorbed onto a polyvinylidene fluoride cartridge and washed with 0.1% TFA. The N-termini of internal peptide fractions were directly sequenced following separation. Edman chemistry was performed on an Applied Biosystems Procise protein sequencer. Amino acids sequentially removed from the N-terminus of each peptide were identified by reverse phase chromatography (Table 1):

TABLE 1

Soybean Phytase Peptide Sequences

| Sample Name | SEQ ID NO: | Amino Acid Sequence |
| --- | --- | --- |
| N-terminus | 4 | HIPSTLEGPFDPVTV |
| peptide 34.466 | 5 | EVGDQIYIVRQPDICPIHQRR |
| peptide 49.745 | 6 | WLERDLENVDRSITPFLDVTIFEV |
| peptide 56.856 | 7 | FCWDRQPDYSAFRESSFGYGILEVK |
| peptide 51.296 | 8 | TVSSVVQYGTSRFELVHEARGQSLIYNQL YPFEGLQXYTSGII |

6.2 Example 2

Isolation and Cloning of Soybean Phytase cDNA 6.21 Reverse Transcription-Polymerase Chain Reaction (RT-PCR)

Total RNA was isolated from soybean cotyledons 9 days after germination using the RNAeasy kit (Qiagen). Oligo-dT primed cDNA was synthesized using Superscript II reverse transcriptase (3' RACE system, Life Technologies). The degenerate upstream primer p49for4 (5'-GCGAYYTNGARAAYGTTGA-3') (SEQ ID NO:9) and the degenerate downstream primer p58rev2 (5'-TCNGGYTGNCKATCCCAACA-3') (SEQ ID NO:10) were designed based on the amino acid sequences of internal peptides 49.745 and 56.856, respectively. A soybean phytase fragment was amplified from the cDNA template using Taq Master Mix (Qiagen). PCR reactions (40 cycles) were performed by denaturation at 94° C. for 30 seconds, annealing at 42° C. for 30 seconds, and extension at 72° C. for 1 minute. The resulting 406 bp fragment was cloned into the SmaI site of pTZ19R (MBI Fermentas, Inc.) and was sequenced using the Sequitherm Excel II kit (Epicenter Technologies). The nucleotide sequence of plasmid pTZ19R is set forth at GenBank/EMBL accession number Y14835, the entire disclosure of which is incorporated herein by reference.

6.22 3' and 5' Rapid Amplification of cDNA Ends (RACE)

Gene-specific primers for amplification of cDNA ends were synthesized based on the nucleotide sequence of the phytase PCR fragment. The 3' end of the phytase cDNA was amplified by nested PCR using the 3' RACE system (Life Technologies). The 3' RACE Adapter Primer and the gene-specific primer phy3' first (5'-ACGAGCCTGGTCATTGTCC-3') (SEQ ID NO:11) were used for first-round PCR amplification from cDNA prepared as described above. PCR conditions (40 cycles) were 94° C. for 30 seconds, 56° C. for 1 minute, and 72° C. for 1 minute. The resulting product served as template for a nested amplification primed by the Abridged Universal Amplification Primer and the gene-specific primer 3'nest (5'-AAGTGAGTAAGTTTTGTTGG-3') (SEQ ID NO:12). PCR conditions (40 cycles) were 94° C. for 30 seconds, 56° C. for 1 minute, and 72° C. for 1 minute. The 520 bp 3' end fragment was cloned into the SmaI site of pTZ19R and sequenced as described above.

A truncated 5' end of the phytase cDNA was amplified using the 5' RACE system (Life Technologies). First strand cDNA synthesis was primed by the gene-specific primer 5' first2 (5'-ACGATCCCAACAAAACTTACTCACTT-3') (SEQ ID NO: 13) using template prepared as described above. The cDNA was tailed according to manufacturer's specifications prior to PCR amplification with the Abridged Anchor Primer and the gene-specific primer 5'nest2 (5'-CAGGAGTACTTAATGGATCGGGACAATGA-3') (SEQ ID NO:14). PCR conditions (40 cycles) were 94° C. for 30 seconds, 50° C. for 30 seconds, and 72° C. for 1.5 minutes. Nested amplification using the Abridged Universal Amplification Primer and the gene-specific primer 5'nest1 (5'-GATCTATCAACATTCTCCAGGTC-3') (SEQ ID NO:15) yielded a 880 bp product which was cloned into the SmaI site of pTZ19R and sequenced as described above.

6.23 Genomic PCR

Genomic DNA was isolated from soybean hypocotyls using the DNAeasy kit (Qiagen) and was used as template for PCR. An upstream degenerate primer phynterm-1 4 (5'-GARGGNCCNITTGATCCCGT-3') (SEQ ID NO:16) was synthesized based on N-terminal amino acid sequence data and a downstream primer 5'first3 (5'-MGGATAGAGCTGGTTGTA GATGA-3') (SEQ ID NO:17) was synthesized based on the RT-PCR product nucleotide sequence. PCR conditions (40 cycles) were 94° C. for 1 minute, 50° C. for 1 minute, and 72° C. for 1 minute. The resulting 646 bp fragment was cloned into the SmaI site of pTZ19R. The cloned DNA repeatedly failed to yield readable sequence, presumably due to secondary structure. The PCR product was digested with restriction enzymes and the resulting fragments were cloned and successfully sequenced. Comparison to previously sequenced cDNA revealed that the fragment contained 315 bp of coding sequence and a 331 bp intron.

6.24 Inverse PCR

Soybean genomic DNA (2 μg) was digested for 1 hour with 40 units XbaI. The enzyme was heat-inactivated and the digested DNA was purified using a Qiaquick spincolumn (Qiagen). The sample was self-ligated in a 1 mL volume at 16° C. overnight. The ligation reaction was purified using a Qiaquick spin-column and was used as template for inverse PCR. The primer Nterm-first (5'-AGAGAAACCGAAATCTGTTC-3') (SEQ ID NO:18) was complementary to the 5' end of the previously amplified genomic fragment with the 3' end of the primer in the direction of the 5' end of the gene. The primer 3'nest (see above) was complementary to a 3' region of the gene downstream of the XhaI site with the 3' end of the primer in the direction of the 3' end of the gene. PCR conditions (40 cycles) were 94° C. for 30 seconds, 54° C. for 1 minute, and 72° C. for 3 minutes. Taq extender (Stratagene) was added to the reaction to facilitate synthesis of long PCR products. The inverse PCR product served as template for nested PCR using the primers Nterm-nest (5'-CGAGGATCGGTTTCCGGCAAGTCG-3') (SEQ ID NO:19) and 3'nest (see above). The resulting 1198 bp product was cloned into the SmaI site of pTZ19R and sequenced as described above. DNA sequence data were obtained for the complete 5' coding region as well as 989 bp of upstream promoter sequence (SEQ ID NO:20).

6.25 Cloning of the Soybean Phytase Coding Sequence Into p35SD

A full-length clone of the soybean phytase coding sequence was generated by high-fidelity PCR. Due to secondary structure near the 5' end of the gene, a portion of the sequence was amplified from genomic DNA and was joined to the remainder of the coding sequence, which was amplified from cDNA, at the EcoRV site. The upstream and downstream primers used to amplify the genomic fragment were 5'ATG-KpnI (5'-CTTTGGTACCATGGCGTCAATTACTTTTTCTC-3') (SEQ ID NO:21) and 5'frst3 (see above), respectively. A KpnI restriction site was included in the upstream primer to facilitate cloning into the final transformation vector. The 802 bp product was generated by 30 cycles of PCR (94° C. for 60 seconds, 50° C. for 30 seconds, 72° C. for 100 seconds) catalyzed by PfuTurbo (Stratagene).

The upstream and downstream primers used to amplify the cDNA fragment were EVupcDNA (5'-CCGTTTGGATATCTTGGGTTAC-3') (SEQ ID NO: 22) and 3' stop-KpnSma (5'-GACCCGGGTACCAATGACAGCAAATGMCT-3') (SEQ ID NO:23), respectively. KpnI and SmaI restriction sites were included in the downstream primer to facilitate cloning into the final transformation vector. The 1428 bp product was generated by 30 cycles of PCR (94° C. for 60 seconds, 50° C. for 30 seconds, 72° C. for 100 seconds) catalyzed by PfuTurbo (Stratagene).

Figure 1B:
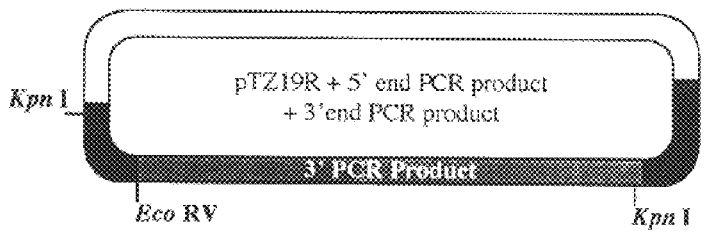
Figure 1C:
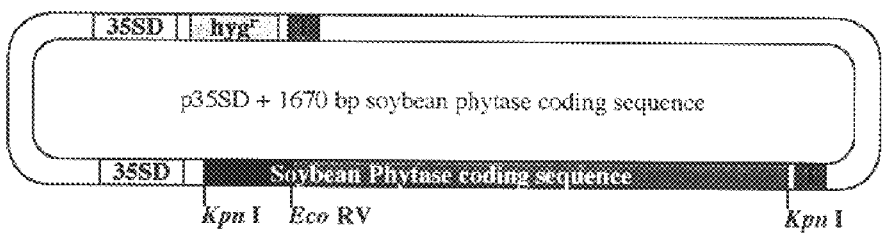
Figure 2:
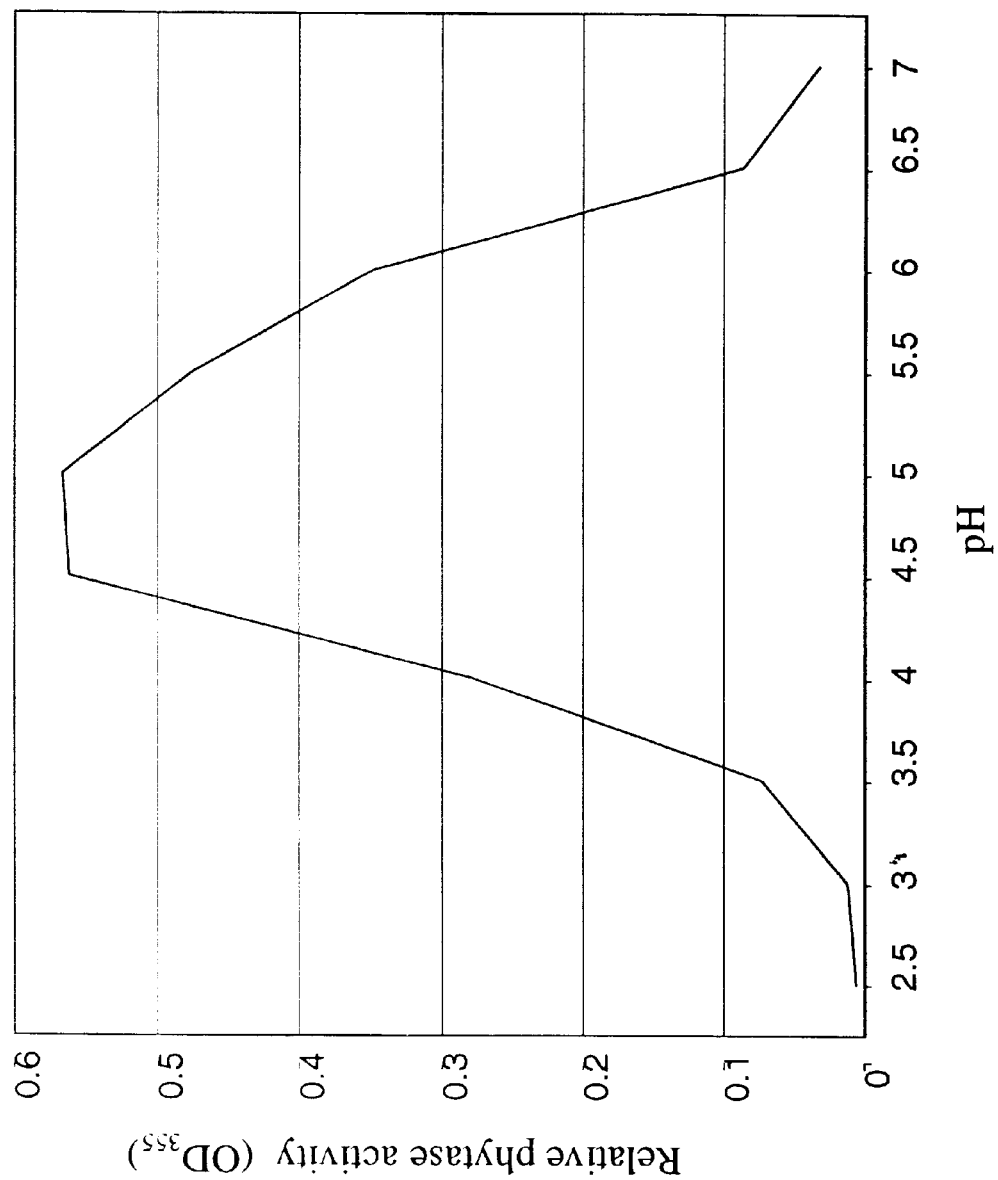
FIG. 2 is a plot of the activity of the purified soybean phytase of the present invention versus pH.

The 802 bp genomic PCR product from the 5' end of the phytase coding sequence was cloned into the SmaI site of PTZ19R (FIG. 1a). The resulting plasmid was digested with EcoRV. The 1.4 kb cDNA PCR product was digested with EcoRV and SmaI and was inserted into the EcoRV digested vector which contained the genomic DNA-derived 5'end (FIG. 1b). The resulting clone was subjected to restriction analysis to verify correct orientation of the insert. The 1670 bp insert was sequenced and a 547 amino acid protein (SEQ ID NO:2) was predicted from the 1644 bp open reading frame (SEQ ID NO:1). All peptide sequences obtained by amino acid sequencing of the phytase protein were present in the translated protein. Protein analysis software (Lasergene) showed that the protein exhibited a molecular weight (62 kD) and pI (5.3) similar to that of the purified phytase enzyme. The predicted isoelectric point of the mature protein is 5.02, with an optimal enzyme activity between pH 4.5 and 5.0.

6.3 Example 3

Preparation of Transformation Vector p35SD

The transformation vector p35SD was derived from the plasmid construct pPHY35P (Li et al., *Plant Physiol.* 114:1103–1111, 1997). Construct pPHY35P contains the constitutive dual-enhanced CaMV 35S promoter which originated from plasmid pRLT2 provided by Dr. J. Mullet, Texas A&M. Plasmid pRLT2, the construction of which is shown in FIG. 3, is a variation of a vector of Carrington and Freed, *J. Virol.* 64:1590–1597 (1990) lacking the gene encoding β-glucuronidase (GUS). In preparing pPHY35P, a portion of the sequence from NcoI to SacI in the promoter of pRLT2 was deleted by endonuclease digestion, generation of blunt ends and religation to eliminate the ATG initiation codon in the NcoI site at the 5' end of the tobacco etch virus (TEV) coding sequence (Li et al., supra).

To generate p35SD from pPHY35P, a fragment containing a KpnI site was inserted at the 3' end of the fungal phytase coding sequence of pPHY35P, allowing for removal of the fungal sequence by KpnI digestion. The new vector designated p35SD was generated by intramolecular ligation of the KpnI ends. The full-length soybean phytase coding sequence was excised from pTZ19R using KpnI and was subcloned into the unique KpnI site of p35SD (FIG. 1c).

6.4 Example 4

Preparation of Transformation Vector pSSP

The transformation vector pSSP was derived from the plasmid construct pPHYSSPss (Li et al., *Plant Physiol.* 114:1103–1111, 1997). The latter is a transformation vector containing a seed specific promoter (α' promoter of the soybean βconglycinin gene). The seed specific expression cassette, containing a multiple cloning site flanked by the α' promoter and terminator in plasmid pUC19, was obtained from Dr. R. Beachy (Chen et al., *Proc. Nat. Acad. Sci. USA* 83:8560–8564, 1986). Prior to use for construction of the pPHYSSPss vector, the multiple cloning site of the α' expression cassette was reversed with respect to the promoter by digesting with BamHI and Bg/II and religating the fragment into the vector. This was done to alter the order of the restriction sites in the multiple cloning site and to eliminate BamHI and Bg/II sites. Sa/I sites flanking the 5' and 3' ends of the fungal phytase sequence allowed removal of the entire fungal phytase coding and signal sequence. Subsequent intramolecular ligation of Sa/I ends was used to create the pSSP vector. The pSSP vector is linearized by digestion with Sa/I and the resulting ends are converted to blunt termini using T4 DNA polymerase for cloning. The full-length soybean phytase coding sequence is excised from pTZ19R using KpnI, treated with T4 DNA polymerase to obtain blunt termini, and blunt-end ligated into the prepared pSSP vector.

6.5 Example 5

Soybean Phytase Vector Transformation of Soybean Embryos and Preparation of Transgenic Soybean Plants The following protocol describes the transformation of soybean embryos with a vector containing the full-length soybean phytase coding sequence, and the generation of transgenic soybean plants characterized by expression of the phytase gene under control of a seed-specific promoter.

Regenerable soybean embryos are initiated from immature cotyledons and maintained in liquid culture or on solid media as previously described (Finer and Nagasawa, *Plant Cell Tiss. Organ Cult.* 15:125–136, 1988; Bailey et al., *In Vitro Cell. Dev. Biol.* 29:102–108, 1993). A phytase construct, e.g., plasmid p35SD or pSSP containing the full-length soybean phytase coding sequence, are introduced by bombardment with the particle inflow gene gun (Finer and McMullen, *In Vitro Cell. Dev. Biol.* 27:175–182, 1991; Finer et al., *Plant Cell Rep.* 11: 323–328, 1992; Bond et al., *Tenn. Farm Home Sci.* 162:4–14, 1992; Vain et al., *Plant Cell, Tissue and Organ Cult.* 33:237–246, 1993). Soybean regeneration is performed as described by Bailey et al., supra. Briefly, soybean embryos are routinely maintained in 10A40N liquid media (MS salts, B5 vitamins, 6% sucrose, 20 mg/ml 2,4 D, 0.2% Gelrite, pH 5.8). Tungsten or gold particles are coated with DNA by $CaCl_2$ precipitation (Finer and McMullen, *Plant Cell Rep.* 8:586–589, 1990). Embryos are bombarded and allowed to recover on MSD20 medium (MS salts, B5 vitamins, 6% sucrose, 20 mg/ml 2,4 D, 0.2% Gelrite, pH 5.8) prior to selection on the same media containing the antibiotic hygromycin (50 µg/ml). Repetitive embryogenic cultures are established from surviving embryos. Development of somatic embryos is accomplished by transfer of globular embryos to MSM6AC auxin-free media (MS salts, B5 vitamins, 6% maltose, 0.5% activated charcoal, 0.2% Gelrite, pH 5.8). Cotyledon stage embryos are transferred to MSM6 maturation media (MS salts, B5 vitamins, 6% maltose, 0.2% Gelrite, pH 5.8), followed by desiccation to improve germination frequencies. Desiccated embryos are transferred to MSO medium (MS salts, B5 vitamins, 3% sucrose, 0.2% Gelrite, pH 5.8) for germination. Plants with roots and primary foliage are transferred to sterile sand:potting mix (1:1) in small pots inside GA-7 Magenta boxes, followed by eventual transfer to the greenhouse for growth of fertile transgenic plants to maturity.

6.6 Example 6

Construction of Binary Vectors for *Agrobacterium tumefaciens*-mediated Transformation The following example describes the preparation of vectors containing the full-length soybean phytase coding sequence, for use in *Agrobacterium tumefaciens*-mediated transformation.

The binary transformation vectors pBIB-KAN-35SD and pBIB-HYG-35SD were generated by inserting a HindIII-KpnI fragment containing the dual-enhanced CaMV 35S promoter into pBIB-KAN and PBIB-HYG vectors (Becker, *Nucleic Acids Res.* 18:203, 1990). The dual-enhanced CaMV 35S promoter originated from plasmid pRLT2. Prior to insertion into the transformation vectors, the NcoI-SacI region of the promoter of the pRLT2 plasmid was removed to eliminate the initiation codon in the NcoI site and the 5' end of the TEV coding sequence. The full-length soybean phytase coding sequence was excised from pTZ19R using KpnI and subcloned into the unique KpnI site of the pBIB-KAN-35SD binary vectors. The same procedure is then used to insert the soybean phytase sequence into pBIB-HYG-35SD.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. An isolated nucleotide sequence encoding a polypeptide comprising the amino acid sequence SEQ ID NO:2 or SEQ ID NO:3, or fragment of SEQ ID NO:3 having phytase activity.

2. An isolated nucleotide sequence selected from the group consisting of:
   (a) SEQ ID NO:1;
   (b) a nucleotide sequence complementary to SEQ ID NO:1;
   (c) a subsequence of SEQ ID NO:1 encoding a polypeptide having phytase activity;
   (d) a nucleotide sequence encoding a polypeptide having phytase activity, which nucleotide sequence hybridizes under conditions of high stringency with (a) or (b), and
   (e) a homologous nucleotide sequence encoding a polypeptide having phytase activity which is at least about 90% homologous with (a) or (b).

3. An expression construct capable of directing the expression of a phytase in a suitable host cell, said expression construct comprising a nucleotide sequence according to claim 1 operably linked to one or more control sequences compatible with said host cell.

4. An expression construct capable of directing the expression of a phytase in a suitable host cell, said expression construct comprising a nucleotide sequence according to claim 2 operably linked to one or more control sequences compatible with said host cell.

5. An expression construct according to claim 3 containing at least one seed-specific expression control element for obtaining expression of said encoding nucleotide sequence in seeds.

6. A host cell transformed with a nucleotide sequence according to claim 1 so that the host cell can express the amino acid sequence encoded by said nucleotide sequence.

7. A host cell transformed with a nucleotide sequence according to claim 2 so that the host cell can express the phytase encoded by said nucleotide sequence.

8. A transformed host cell according to claim 6 wherein the host cell is a eukaryote.

9. A transformed host cell according to claim 8 wherein the host cell is a plant cell.

10. A method for producing a soybean phytase comprising:
    growing a culture of transformed host cells of claim 6 under conditions conducive to the expression of said phytase by said host cells.

11. A method for producing a soybean phytase comprising growing a culture of transformed host cells of claim 7 under conditions conducive to the expression of said phytase by said host cells.

12. An expression construct according to claim 4 containing at least one seed-specific expression control element for obtaining expression of said encoding nucleotide sequence in seeds.

13. A transformed host cell according to claim 7 wherein the host cell is a eukaryote.

14. A transformed host cell according to claim 13 wherein the host cell is a plant cell.

15. An isolated nucleotide sequence according to claim 1 wherein the fragment of SEQ ID NO:3 having phytase activity contains least 100 amino acids.

16. An isolated nucleotide sequence according to claim 1 wherein the fragment of SEQ ID NO:3 having phytase activity contains least 250 amino acids.

17. An isolated nucleotide sequence according to claim 1 wherein the fragment of SEQ ID NO:3 having phytase activity contains least 500 amino acids.

18. An isolated nucleotide sequence according to claim 2 wherein the subsequences of SEQ ID NO: 1 encoding a polypeptide having phytase activity contain at least 900 nucleotides.

19. An isolated nucleotide sequence according to claim 2 wherein the subsequences of SEQ ID NO: 1 encoding a polypeptide having phytase activity contain at least 1200 nucleotides.

20. An isolated nucleotide sequence according to claim 2 wherein the subsequences of SEQ ID NO: 1 encoding a polypeptide having phytase activity contain at least 1500 nucleotides.

* * * * *

SEQUENCE LISTING

```
<160> NUMBER OF SEQ ID NOS:  24

<210> SEQ ID NO 1
<211> LENGTH: 1644
<212> TYPE: DNA
<213> ORGANISM: Glycine max

<400> SEQUENCE: 1
atggcgtcaa ttactttttc tcttcttcaa tttcatcgtg ctcctattct tctgctaatt      60
ctgctcgcgg gtttcggtca ctgccatatt ccgtcaaccc tcgaaggtcc ctttgatccc     120
gtcaccgttc cgttcgaccc cgccttgcgc ggcgtcgccg tcgacttgcc ggaaaccgat     180
cctcgagttc gccgccgcgt ccggggtttc gagcccgaac agatttcggt ttctctctct     240
acctcccatg actccgtttg gatatcttgg gttacagggg agttccaaat aggtctcgac     300
atcaagcctt tagaccctaa aactgtatca agtgttgttc aatatggaac ttcaagattt     360
gaattagtgc atgaagctag aggccagtct ctcatctaca accagctcta tccttttgaa     420
ggccttcaga attacacatc tggaatcatc catcacgttc aactcaaagg attggaacca     480
agcacactat actattatca atgtggagat ccttcattgc aagccatgag tgatatatac     540
tatttcagga ccatgccaat ttctggttca aagagctacc caggcaaagt agctgtagta     600
ggagatcttg gtcttactta taatacaact actaccatcg gtcacctgac tagtaatgaa     660
cctgatcttc ttctattgat tggtgatgta acctacgcga atctgtacct cacaaatgga     720
actggctctg attgttatag ttgctcgttt ccactaactc ctatacatga aacctaccag     780
cctcgatggg attattgggg aaggtttatg cagaatctag tttctaacgt tccaataatg     840
gtggtagaag gaaatcatga aatagaaaaa caggctgaaa acaggacatt tgtggcctac     900
agttctaggt ttgcattccc ctctcaagaa agtggatctt catctacatt ctactattct     960
ttcaatgctg gaggcattca tttattatg cttggggctt atattaacta tgataaaacg    1020
gctgaacaat acaagtggtt ggagagagat ctggaaaatg ttgatagatc aataactccc    1080
```

-continued

```
tggcttgtag ttacttggca tccaccatgg tatagttctt atgaagccca ttacagagaa    1140
gcagagtgca tgagggtgga gatggaggac ctattatacg catatggtgt ggatataata    1200
tttaatggac atgttcatgc ctatgagagg tcaaaccgag tttacaatta caatttagat    1260
ccatgtggtc ctgtatatat tacagttggg gatgggggca acagagagaa gatggcaatc    1320
aaattcgcag acgagcctgg tcattgtccc gatccattaa gtactcctga tcctttatatg   1380 ggtggctttt gtgcaacaaa ttttacgttt ggtacaaaag tgagtaagtt ttgttgggat    1440
cgccagccag attacagtgc tttcagagaa agtagctttg gctatgggat tctagaggtg    1500
aaaaatgaaa cttgggcttt gtggagttgg tatcgtaatc aggactctta caaggaagtt    1560
ggggatcaaa tttacatagt gagacaacct gatatatgcc ccatccatca aagggtgaac    1620
atagattgca ttgcttcgat ataa                                          1644
```

<210> SEQ ID NO 2
<211> LENGTH: 547
<212> TYPE: PRT
<213> ORGANISM: Glycine max

<400> SEQUENCE: 2

```
Met Ala Ser Ile Thr Phe Ser Leu Leu Gln Phe His Arg Ala Pro Ile
 1               5                  10                  15

Leu Leu Leu Ile Leu Leu Ala Gly Phe Gly His Cys His Ile Pro Ser
             20                  25                  30

Thr Leu Glu Gly Pro Phe Asp Pro Val Thr Val Pro Phe Asp Pro Ala
         35                  40                  45

Leu Arg Gly Val Ala Val Asp Leu Pro Glu Thr Asp Pro Arg Val Arg
     50                  55                  60

Arg Arg Val Arg Gly Phe Glu Pro Glu Gln Ile Ser Val Ser Leu Ser
 65                  70                  75                  80

Thr Ser His Asp Ser Val Trp Ile Ser Trp Val Thr Gly Glu Phe Gln
                 85                  90                  95

Ile Gly Leu Asp Ile Lys Pro Leu Asp Pro Lys Thr Val Ser Ser Val
            100                 105                 110

Val Gln Tyr Gly Thr Ser Arg Phe Glu Leu Val His Glu Ala Arg Gly
        115                 120                 125

Gln Ser Leu Ile Tyr Asn Gln Leu Tyr Pro Phe Glu Gly Leu Gln Asn
    130                 135                 140

Tyr Thr Ser Gly Ile Ile His His Val Gln Leu Lys Gly Leu Glu Pro
145                 150                 155                 160

Ser Thr Leu Tyr Tyr Tyr Gln Cys Gly Asp Pro Ser Leu Gln Ala Met
                165                 170                 175

Ser Asp Ile Tyr Tyr Phe Arg Thr Met Pro Ile Ser Gly Ser Lys Ser
            180                 185                 190

Tyr Pro Gly Lys Val Ala Val Val Gly Asp Leu Gly Leu Thr Tyr Asn
        195                 200                 205

Thr Thr Thr Ile Gly His Leu Thr Ser Asn Glu Pro Asp Leu Leu
    210                 215                 220

Leu Leu Ile Gly Asp Val Thr Tyr Ala Asn Leu Tyr Leu Thr Asn Gly
225                 230                 235                 240

Thr Gly Ser Asp Cys Tyr Ser Cys Ser Phe Pro Leu Thr Pro Ile His
                245                 250                 255

Glu Thr Tyr Gln Pro Arg Trp Asp Tyr Trp Gly Arg Phe Met Gln Asn
            260                 265                 270
```

-continued

```
Leu Val Ser Asn Val Pro Ile Met Val Val Glu Gly Asn His Glu Ile
        275                 280                 285
Glu Lys Gln Ala Glu Asn Arg Thr Phe Val Ala Tyr Ser Ser Arg Phe
    290                 295                 300
Ala Phe Pro Ser Gln Glu Ser Gly Ser Ser Thr Phe Tyr Tyr Ser
305                 310                 315                 320
Phe Asn Ala Gly Gly Ile His Phe Ile Met Leu Gly Ala Tyr Ile Asn
                325                 330                 335
Tyr Asp Lys Thr Ala Glu Gln Tyr Lys Trp Leu Glu Arg Asp Leu Glu
            340                 345                 350
Asn Val Asp Arg Ser Ile Thr Pro Trp Leu Val Thr Trp His Pro
        355                 360                 365
Pro Trp Tyr Ser Ser Tyr Glu Ala His Tyr Arg Glu Ala Cys Met
    370                 375                 380
Arg Val Glu Met Glu Asp Leu Leu Tyr Ala Tyr Gly Val Asp Ile Ile
385                 390                 395                 400
Phe Asn Gly His Val His Ala Tyr Glu Arg Ser Asn Arg Val Tyr Asn
                405                 410                 415
Tyr Asn Leu Asp Pro Cys Gly Pro Val Tyr Ile Thr Val Gly Asp Gly
            420                 425                 430
Gly Asn Arg Glu Lys Met Ala Ile Lys Phe Ala Asp Glu Pro Gly His
        435                 440                 445
Cys Pro Asp Pro Leu Ser Thr Pro Asp Pro Tyr Met Gly Gly Phe Cys
    450                 455                 460
Ala Thr Asn Phe Thr Phe Gly Thr Lys Val Ser Lys Phe Cys Trp Asp
465                 470                 475                 480
Arg Gln Pro Asp Tyr Ser Ala Phe Arg Glu Ser Ser Phe Gly Tyr Gly
                485                 490                 495
Ile Leu Glu Val Lys Asn Glu Thr Trp Ala Leu Trp Ser Trp Tyr Arg
            500                 505                 510
Asn Gln Asp Ser Tyr Lys Glu Val Gly Asp Gln Ile Tyr Ile Val Arg
        515                 520                 525
Gln Pro Asp Ile Cys Pro Ile His Gln Arg Val Asn Ile Asp Cys Ile
    530                 535                 540
Ala Ser Ile
545

<210> SEQ ID NO 3
<211> LENGTH: 519
<212> TYPE: PRT
<213> ORGANISM: Glycine max

<400> SEQUENCE: 3

His Ile Pro Ser Thr Leu Glu Gly Pro Phe Asp Pro Val Thr Val Pro
  1               5                  10                  15
Phe Asp Pro Ala Leu Arg Gly Val Ala Val Asp Leu Pro Glu Thr Asp
                20                  25                  30
Pro Arg Val Arg Arg Arg Val Arg Gly Phe Glu Pro Glu Gln Ile Ser
            35                  40                  45
Val Ser Leu Ser Thr Ser His Asp Ser Val Trp Ile Ser Trp Val Thr
        50                  55                  60
Gly Glu Phe Gln Ile Gly Leu Asp Ile Lys Pro Leu Asp Pro Lys Thr
65                  70                  75                  80
Val Ser Ser Val Val Gln Tyr Gly Thr Ser Arg Phe Glu Leu Val His
```

-continued

```
                        85                  90                  95
Glu Ala Arg Gly Gln Ser Leu Ile Tyr Asn Gln Leu Tyr Pro Phe Glu
                100                 105                 110
Gly Leu Gln Asn Tyr Thr Ser Gly Ile Ile His His Val Gln Leu Lys
                115                 120                 125
Gly Leu Glu Pro Ser Thr Leu Tyr Tyr Gln Cys Gly Asp Pro Ser
            130                 135                 140
Leu Gln Ala Met Ser Asp Ile Tyr Tyr Phe Arg Thr Met Pro Ile Ser
145                 150                 155                 160
Gly Ser Lys Ser Tyr Pro Gly Lys Val Ala Val Gly Asp Leu Gly
                165                 170                 175
Leu Thr Tyr Asn Thr Thr Thr Thr Ile Gly His Leu Thr Ser Asn Glu
                180                 185                 190
Pro Asp Leu Leu Leu Ile Gly Asp Val Thr Tyr Ala Asn Leu Tyr
                195                 200                 205
Leu Thr Asn Gly Thr Gly Ser Asp Cys Tyr Ser Cys Ser Phe Pro Leu
            210                 215                 220
Thr Pro Ile His Glu Thr Tyr Gln Pro Arg Trp Asp Tyr Trp Gly Arg
225                 230                 235                 240
Phe Met Gln Asn Leu Val Ser Asn Val Pro Ile Met Val Val Glu Gly
                245                 250                 255
Asn His Glu Ile Glu Lys Gln Ala Glu Asn Arg Thr Phe Val Ala Tyr
                260                 265                 270
Ser Ser Arg Phe Ala Phe Pro Ser Gln Glu Ser Gly Ser Ser Ser Thr
                275                 280                 285
Phe Tyr Tyr Ser Phe Asn Ala Gly Gly Ile His Phe Ile Met Leu Gly
            290                 295                 300
Ala Tyr Ile Asn Tyr Asp Lys Thr Ala Glu Gln Tyr Lys Trp Leu Glu
305                 310                 315                 320
Arg Asp Leu Glu Asn Val Asp Arg Ser Ile Thr Pro Trp Leu Val Val
                325                 330                 335
Thr Trp His Pro Pro Trp Tyr Ser Ser Tyr Glu Ala His Tyr Arg Glu
                340                 345                 350
Ala Glu Cys Met Arg Val Glu Met Glu Asp Leu Leu Tyr Ala Tyr Gly
            355                 360                 365
Val Asp Ile Ile Phe Asn Gly His Val His Ala Tyr Glu Arg Ser Asn
370                 375                 380
Arg Val Tyr Asn Tyr Asn Leu Asp Pro Cys Gly Pro Val Tyr Ile Thr
385                 390                 395                 400
Val Gly Asp Gly Gly Asn Arg Glu Lys Met Ala Ile Lys Phe Ala Asp
                405                 410                 415
Glu Pro Gly His Cys Pro Asp Pro Leu Ser Thr Pro Asp Pro Tyr Met
                420                 425                 430
Gly Gly Phe Cys Ala Thr Asn Phe Thr Phe Gly Thr Lys Val Ser Lys
            435                 440                 445
Phe Cys Trp Asp Arg Gln Pro Asp Tyr Ser Ala Phe Arg Glu Ser Ser
    450                 455                 460
Phe Gly Tyr Gly Ile Leu Glu Val Lys Asn Glu Thr Trp Ala Leu Trp
465                 470                 475                 480
Ser Trp Tyr Arg Asn Gln Asp Ser Tyr Lys Glu Val Gly Asp Gln Ile
                485                 490                 495
Tyr Ile Val Arg Gln Pro Asp Ile Cys Pro Ile His Gln Arg Val Asn
                500                 505                 510
```

```
Ile Asp Cys Ile Ala Ser Ile
          515
```

<210> SEQ ID NO 4
<211> LENGTH: 15
<212> TYPE: PRT
<213> ORGANISM: Glycine max

<400> SEQUENCE: 4

```
His Ile Pro Ser Thr Leu Glu Gly Pro Phe Asp Pro Val Thr Val
 1               5                  10                  15
```

<210> SEQ ID NO 5
<211> LENGTH: 21
<212> TYPE: PRT
<213> ORGANISM: Glycine max

<400> SEQUENCE: 5

```
Glu Val Gly Asp Gln Ile Tyr Ile Val Arg Gln Pro Asp Ile Cys Pro
 1               5                  10                  15

Ile His Gln Arg Arg
            20
```

<210> SEQ ID NO 6
<211> LENGTH: 24
<212> TYPE: PRT
<213> ORGANISM: Glycine max

<400> SEQUENCE: 6

```
Trp Leu Glu Arg Asp Leu Glu Asn Val Asp Arg Ser Ile Thr Pro Phe
 1               5                  10                  15

Leu Asp Val Thr Ile Phe Glu Val
            20
```

<210> SEQ ID NO 7
<211> LENGTH: 25
<212> TYPE: PRT
<213> ORGANISM: Glycine max

<400> SEQUENCE: 7

```
Phe Cys Trp Asp Arg Gln Pro Asp Tyr Ser Ala Phe Arg Glu Ser Ser
 1               5                  10                  15

Phe Gly Tyr Gly Ile Leu Glu Val Lys
            20                  25
```

<210> SEQ ID NO 8
<211> LENGTH: 43
<212> TYPE: PRT
<213> ORGANISM: Glycine max
<220> FEATURE:
<221> NAME/KEY: UNSURE
<222> LOCATION: (37)
<223> OTHER INFORMATION: unknown amino acid

<400> SEQUENCE: 8

```
Thr Val Ser Ser Val Val Gln Tyr Gly Thr Ser Arg Phe Glu Leu Val
 1               5                  10                  15

His Glu Ala Arg Gly Gln Ser Leu Ile Tyr Asn Gln Leu Tyr Pro Phe
            20                  25                  30

Glu Gly Leu Gln Xaa Tyr Thr Ser Gly Ile Ile
        35                  40
```

```
<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Degenerate
      upstream primer
<221> NAME/KEY: modified_base
<222> LOCATION: (8)
<223> OTHER INFORMATION: a, t, c, or g

<400> SEQUENCE: 9
gcgayytnga raaygttga                                                     19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Degenerate
      downstream primer
<221> NAME/KEY: modified_base
<222> LOCATION: (3)
<223> OTHER INFORMATION: a, t, c or g
<221> NAME/KEY: modified_base
<222> LOCATION: (9)
<223> OTHER INFORMATION: a, t, c or g

<400> SEQUENCE: 10
tcnggytgnc katcccaaca                                                    20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:
      Gene-specific primer

<400> SEQUENCE: 11
acgagcctgg tcattgtcc                                                     19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      Gene-specific primer

<400> SEQUENCE: 12
aagtgagtaa gttttgttgg                                                    20

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:
      Gene-specific primer

<400> SEQUENCE: 13
acgatcccaa caaaacttac tcactt                                             26

<210> SEQ ID NO 14
<211> LENGTH: 29
<212> TYPE: DNA
<213> ORGANISM: Artificial Sequence
<220> FEATURE:
```

```
<223> OTHER INFORMATION: Description of Artificial Sequence:
      Gene-specific primer

<400> SEQUENCE: 14
caggagtact taatggatcg ggacaatga                                              29

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:
      Gene-specific primer

<400> SEQUENCE: 15
gatctatcaa cattctccag gtc                                                    23

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Upstream
      degenerate primer
<221> NAME/KEY: modified_base
<222> LOCATION: (6)
<223> OTHER INFORMATION: a, t, c or g
<221> NAME/KEY: modified_base
<222> LOCATION: (9)
<223> OTHER INFORMATION: a, t, c or g

<400> SEQUENCE: 16
garggnccnt ttgatcccgt                                                        20

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Downstream
      degenerate primer

<400> SEQUENCE: 17
aaggatagag ctggttgtag atga                                                   24

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Inverse PCR
      primer

<400> SEQUENCE: 18
agagaaaccg aaatctgttc                                                        20

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Inverse PCR
      primer

<400> SEQUENCE: 19
cgaggatcgg tttccggcaa gtcg                                                   24
```

<210> SEQ ID NO 20
<211> LENGTH: 989
<212> TYPE: DNA
<213> ORGANISM: Glycine max

<400> SEQUENCE: 20

```
tctagaattc aaattaaaaa cttaatttca actaaaagaa caatatgtcc atagacaaca      60
aggcaaaaca aaacttttgc ttacaagtgt gatctcaatg ttcttgaaat taaatttaca     120
tgcgtactgt gtatttaaag acttcatcga atggttattt tcgctaaaaa atctaattaa     180
tcacctctaa taaaaaatta attatatttc tttttatcca caatagtcaa atttaaaatt     240
tacttaagat gactaaattc agtgtcactt agcccaacag ttaaacttag aattagttaa     300
acttagaatt tacttaaaat cattaagtct agtgtcactt agtccaacat cttattatcg     360
atagagttta acctaaagaa atagatgaag agatagagtt aaggaaataa aaacaactaa     420
aaagagttga gaaaaaacaa aaaaaagtcg tatgttcaat ctactttgac ggagaaaaat     480
gatcttaaga acttgaaata gaagaccaag attcatgaac tggttttaag gcaaatagga     540
gtagcaaatt ggaatggttg tccaataggt aataatcttg cctctcaatc acatgtgtca     600
cttaggcacg tctgaattaa aattttgtaa agctatcgta agtcttactc cttctttttaa    660
attgagtttg catgtaaaac tttactcttg aacatatttt taaggtggaa ccaaacatac     720
cctaaggatt tcaaagagat tatatttcag attatcttct tttggccaat tctgattctc     780
tttggttaaa aaaatgatag tataaaatta aaactgccac gtgacgttcc cacggcaaag    840
ccttctgtac tcttacactg tcagtctcag tctcagttcc agttccaagt ataaccgtac     900
tctccacttc tttttacttt ctcacacgca accaaatcca tccgtttcaa caaacacaaa     960
attacgttcc gcgtttggat tctccaatg                                       989
```

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Upstream
      primer

<400> SEQUENCE: 21

```
ctttggtacc atggcgtcaa ttactttttc tc                                    32
```

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Upstream
      primer

<400> SEQUENCE: 22

```
ccgtttggat atcttgggtt ac                                               22
```

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Downstream
      primer

<400> SEQUENCE: 23

```
gacccgggta ccaatgacag caaatgaact                                       30
```

```
<210> SEQ ID NO 24
<211> LENGTH: 28
<212> TYPE: PRT
<213> ORGANISM: Glycine max

<400> SEQUENCE: 24

Met Ala Ser Ile Thr Phe Ser Leu Leu Gln Phe His Arg Ala Pro Ile
 1               5                  10                  15

Leu Leu Leu Ile Leu Leu Ala Gly Phe Gly His Cys
            20                  25
```